US010943684B2

United States Patent
Leedy

(10) Patent No.: US 10,943,684 B2
(45) Date of Patent: Mar. 9, 2021

(54) METHODS AND SYSTEMS FOR ELECTRONIC PRESCRIPTION BASED ETASU ENFORCEMENT

(71) Applicant: Jason Leedy, Haverford, PA (US)

(72) Inventor: Jason Leedy, Haverford, PA (US)

(73) Assignee: Jason Leedy, Haverford, PA (US)

(*) Notice: Subject to any disclaimer, the term of this patent is extended or adjusted under 35 U.S.C. 154(b) by 85 days.

(21) Appl. No.: 16/022,141

(22) Filed: Jun. 28, 2018

(65) Prior Publication Data
US 2019/0006034 A1 Jan. 3, 2019

Related U.S. Application Data

(60) Provisional application No. 62/526,222, filed on Jun. 28, 2017.

(51) Int. Cl.
| | |
|---|---|
| *G16H 20/10* | (2018.01) |
| *G16H 80/00* | (2018.01) |
| *G06Q 50/22* | (2018.01) |
| *G16H 70/40* | (2018.01) |

(52) U.S. Cl.
CPC ............ *G16H 20/10* (2018.01); *G16H 70/40* (2018.01); *G16H 80/00* (2018.01); *G06Q 50/22* (2013.01)

(58) Field of Classification Search
CPC .......... G06F 19/32; G06F 19/34; G06F 21/62; G06Q 10/10; G06Q 50/22; G06Q 50/24; G16H 10/60; G16H 20/10; G16H 40/20; G16H 40/63; G16H 80/00; G16H 70/40;
(Continued)

(56) References Cited

U.S. PATENT DOCUMENTS

| 8,386,274 B1* | 2/2013 | Pinsonneault | ...... G06F 19/3456 |
|---|---|---|---|
| | | | 705/2 |
| 8,392,219 B1* | 3/2013 | Pinsonneault | ......... G06Q 50/22 |
| | | | 705/3 |

(Continued)

OTHER PUBLICATIONS

Rothermich, Phillip A.; Swanson, Terri A. "Electronic Prescribing Security and Authentication." Dec. 9, 2004. Express Scripts, Inc. and CIGNA Pharmacy Management. Slideshow. (Year: 2004).*

(Continued)

*Primary Examiner* — Christopher L Gilligan
*Assistant Examiner* — Chance L Smith
(74) *Attorney, Agent, or Firm* — Invention Mine LLC

(57) ABSTRACT

Utilizing electronic prescriptions (eRx), ETASU enforcement for a drug associated with a REMS may be performed at a more natural point in prescription processing. By incorporating an encrypted REMS Dispense Authorization (RDA) into eRxs, an eRx router may validate various elements of the eRx against encrypted data elements and thereby verify that any ETASUs required by a REMS for a prescribed drug have been complied with. As a result, only validated eRx are passed from the eRx router to pharmacies for dispensing, reducing manual intervention to confirm compliance. Information necessary to perform validation may be communicated to the eRx router by a Trusted Central RDA Authority (TCRA), and may include decryption keys, prescriber authorization data, and appropriate validation check algorithms.

19 Claims, 12 Drawing Sheets

(58) Field of Classification Search
CPC .... H04L 2209/88; H04L 63/04; H04W 12/02; H04W 12/06
See application file for complete search history.

(56) References Cited

U.S. PATENT DOCUMENTS

| | | | | |
|---|---|---|---|---|
| 8,626,529 | B1* | 1/2014 | Pinsonneault | G06Q 10/0635 705/2 |
| 9,734,541 | B1* | 8/2017 | Pinsonneault | G06Q 50/22 |
| 10,496,793 | B1* | 12/2019 | Lawrence | G06Q 50/22 |
| 2002/0038420 | A1* | 3/2002 | Collins | H04L 9/3263 713/156 |
| 2003/0088771 | A1* | 5/2003 | Merchen | G06F 21/6245 713/175 |
| 2004/0002872 | A1* | 1/2004 | Wright | G06F 19/3418 705/2 |
| 2005/0209879 | A1* | 9/2005 | Chalmers | G06Q 50/22 705/2 |
| 2006/0259330 | A1* | 11/2006 | Schranz | G06F 19/328 705/3 |
| 2008/0222042 | A1* | 9/2008 | Moore | G06F 19/3456 705/55 |
| 2009/0198520 | A1* | 8/2009 | Piovanetti-Perez | G06Q 10/06375 705/3 |
| 2011/0145018 | A1* | 6/2011 | Fotsch | G06F 19/326 705/3 |
| 2012/0036368 | A1* | 2/2012 | Spalka | G06F 21/34 713/182 |
| 2012/0087494 | A1* | 4/2012 | Spalka | H04L 9/0825 380/46 |
| 2013/0179177 | A1* | 7/2013 | Dhavle | G06Q 30/0601 705/2 |
| 2013/0191139 | A1* | 7/2013 | Chen | G06F 19/3456 705/2 |
| 2013/0231945 | A1* | 9/2013 | Barry | G06F 19/3456 705/2 |
| 2013/0297333 | A1* | 11/2013 | Timmons | G06F 19/3456 705/2 |
| 2013/0339044 | A1* | 12/2013 | Sheehan | G06Q 10/0635 705/2 |
| 2014/0249832 | A1* | 9/2014 | Link | G06F 19/00 705/2 |
| 2015/0112723 | A1* | 4/2015 | Holt | G06F 19/3456 705/3 |
| 2015/0371001 | A1* | 12/2015 | Pinsonneault | G06F 19/3456 705/2 |
| 2017/0337346 | A1* | 11/2017 | Goel | G06F 19/3456 |
| 2018/0358117 | A1* | 12/2018 | Neagle | A61B 5/742 |
| 2020/0005919 | A1* | 1/2020 | Hill, Sr. | G06F 16/2358 |

OTHER PUBLICATIONS

Service Objects. "How IP Validation Can Help Prevent Fraud." Dec. 29, 2015. Service Objects. Website. https://www.serviceobjects.com/blog/how-ip-validation-can-help-prevent-fraud/ (Year: 2015).*

"Electronic Code of Federal Regulations." Title 45, Subtitle A, Subchapter C, Part 164, Subpart C, Statute 164.312. Feb. 20, 2003, amended Jan. 25, 2013. Federal law and website. https://www.ecfr.gov/cgi-bin/retrieveECFR?n=sp45.1.164.c#se45.1.164_1306 (Year: 2013).*

Office for Civil Rights. "Is the use of encryption mandatory in the Security Rule?" Jul. 26, 2013. U.S. Department of Health & Human Services. Website. https://www.hhs.gov/hipaa/for-professionals/faq/2001/is-the-use-of-encryption-mandatory-in-the-security-rule/index.html (Year: 2013).*

* cited by examiner

```
// Check Pseudo Code
// Define:
drugList        // n number of drug IDs and associated private crypto keys
approvedIDPair  // Pairs of FRO IDs and eRx network IDs
networkScript   // The health networks xml based eRx
network         // Object representing the Health Network, e.g., eRx router
xmlRDA          // Object representation of the decrypted RDA //get Crypto Key for drug
Func getKey(uniqueDrugID) {Return CrypotKey from drugList based on uniqueDrugID}

// return script to sender, e.g., pharmacy
returnScript(message){
   // have script network return script to originator with rejection notice
   network.ReturnScript(networkScript, message)}

// Main
For Each networkScript {
   // Is this prescription part of the REMS
   If networkScript.UniqueDrugID is in drugList {
      //Can we decrypt it with this REMS key pair
      If (let xmlRDA = Decrypt( networkScript.RDA, getKey( networkScript.UniqueDrugID ))) {
         // Is it the certified originator on file
         If xmlRDA.federatedRDAUniqueID = approvedIDPair( networkScript.UniqueDrugID ) {
            // Does the RDA match the Rx: doctor, patient, etc.
            If xmlRDA.data == networkScript.data {
               // Has this Rx expired
               If now() between xmlRDA.effectiveDateStart and xmlRDA.effectiveDateEnd {
                  network.release(networkScript) // RDA ensuring ETASU present – send to Pharmacy
               }
               Else { returnScript("Error: RDA is expired.")  }
            }
            Else {returnScript("Error: RDA does not match Script.")}
         }
         Else {returnScript("Error: Spoofing underway.")}
      }
      Else {returnScript("RDA Encryption Error.")}
   }
   Else {//network Rx passes to Pharmacy, is not a drug under REMS
      network.release(networkScript)}
}
```

FIG. 8

METHODS AND SYSTEMS FOR ELECTRONIC PRESCRIPTION BASED ETASU ENFORCEMENT

CROSS-REFERENCE TO RELATED APPLICATIONS

The present application is a non-provisional filing which claims benefit under 35 U.S.C. § 119(e) from, U.S. Provisional Patent Application Ser. No. 62/526,222, filed Jun. 28, 2017, entitled "METHODS AND SYSTEMS FOR ELECTRONIC PRESCRIPTION BASED ETASU ENFORCEMENT", which is incorporated herein by reference in its entirety.

BACKGROUND

Risk Evaluation and Mitigation Strategies (REMS) are FDA required risk management plans. The plans mandate risk minimization strategies beyond professional labeling to ensure that the benefits of certain prescription drugs outweigh their risks. There are several risk types including but not limited to serious infection, severe allergic reaction, liver damage, and severe birth defects.

If the FDA determines a REMS is necessary to ensure that the benefits of the drug outweigh the risk, the FDA may require a REMS before drug approval. If, post-approval, the FDA becomes aware of new safety information, the FDA may determine that a REMS is necessary to ensure that the benefits of the drug outweigh the risks.

Elements to Assure Safe Use (ETASU) are specific mandated components of a REMS. ETASUs are required medical interventions or other actions healthcare professionals need to execute prior to prescribing or dispensing the drug to the patient. Some actions may also be required for the patient to continue treatment. A Hard Stop is a systematic way to prohibit a REMS drug from being dispensed when the ETASUs are not satisfied for a patient at a specific time, i.e. the fill or refill of the prescription.

Generally, a REMS is operated by a REMS Administrator, an entity that is responsible for implementing and operating the REMS as approved by the FDA. The REMS Administrator is often either a single drug manufacturer or an entity made up of several vendors—such as a call center, IT Solutions, Drug Safety, Project Management Office, etc.— acting on behalf of either a single drug manufacturer or group of drug manufacturers.

For drugs associated with a REMS, there may be a REMS Dispense Authorization (RDA) (also alternatively known as a risk management authorization, a pre-dispense authorization, a prior authorization or "prior-auth", etc.). An RDA may be a unique number or code that is provided to a pharmacy that represents an authorization by the REMS Administrator for the patient to receive the drug at the time of the inquiry.

REMS can vary greatly in both size and complexity. The simplest REMS may only require a medication guide which is an educational component for a stakeholder. Other REMS may also include a communication plan, ETASUs, and an implementation system. The most complicated REMS via their various ETASUs may often mandate, for example: educational components for stakeholders; comprehension testing; documented healthcare provider counseling of patients; specific patient lab testing; a required, specific sequence and timing of the various ETASUs; a Hard Stop at the pharmacy (e.g., a systematic way to prohibit a REMS drug from being dispensed when the ETASUs are not satisfied for a patient at a specific time, i.e., the fill or refill of the prescription); an implementation system; interfaces into other healthcare IT solutions and networks; live call center support; a pregnancy registry; and/or the like.

A complicated REMS system may have a very large implementation system that manages processes, collects data, and interfaces with many other systems.

Payment Based ETASU Enforcement. To date, REMS have generally relied on the interaction of a patient and their pharmacy as the point in the patient care process for enforcement of ETASUs. This enforcement has been executed in two ways. Initially, REMS programs relied on a pharmacist to attest to the requirement of manually checking with a call center, an interactive voice response system, or a website for an RDA before dispensing the drug. Alternatively, some current REMs programs are being required to implement a Hard Stop.

The payment based Hard Stop has become the preferred method as it may remove the potential for human noncompliance, and may reduce burden on the pharmacy by integrating ETASU enforcement into the pharmacy workflow. The current and only Hard Stop in the marketplace is implemented inside the process of financial adjudication of prescription drug claims. One embodiment of an existing process is described in U.S. Pat. No. 8,626,529.

FIG. 1 depicts the process and the point of enforcement at a high level. A healthcare provider (105) may generate either an electronic prescription (eRx) (112) or a traditional paper prescription (110) for a patient (115). A patient will receive the paper prescription to take to a pharmacist (120), while an eRx (112) is transmitted directly to a pharmacy/pharmacist (120). The pharmacist (120) may then process a prescription (either paper or eRx), for example by communicating with a financial adjudication system (125). During the adjudication (which would normally involve the financial adjudication system (125) to coordinate with one or more payers (135a, 135b, etc.)), a hard stop (127) may be implemented. During the hard stop, a REMS Administrator or REMS Administrator system (130) may enforce any relevant ETASUs, through communication (132) with the financial adjudication system (125), and perhaps with a pharmacy or pharmacist (120).

While the FDA has made clear that they believe that the payment based Hard Stop is superior to the manual method for pharmacy enforcement of ETASUs, this process has many shortcomings. Primarily, the ETASU enforcement happens late in the patient care process. In a REMS with ETASUs that are required by the prescriber and the patient, this may cause confusion and rework. This type of Hard Stop may also be problematic when a prescriber and patient believe they have met the ETASUs and collaborate to fill the prescription (e.g., review the medication information, select the appropriate drug and dosing, write the prescription, travel to the pharmacy for pickup, present insurance, etc.), only to find out that the drug cannot be dispensed. It can cause rework, additional costs, and inconvenience(s). Additionally, if this occurs within a REMS that has an ETASU based on a required timing of a sequence of events, the negative impact may be worse than inconvenience and cost, as it may affect access to the drug. Dispensing of the drug may be prohibited because the patient may not have sufficient time to rectify any of the missing ETASUs, thus requiring the patient and/or doctor to restart the REMS process. In addition, the co-mingling of insurance reasons for rejecting the fill of prescription and safety reasons can be less than clear for both the pharmacist and the patient.

The systems and methods disclosed herein address these issues, and others.

SUMMARY

Described herein are systems and methods related to an e-prescription (eRx) based ETASU enforcement model. These systems and methods may eliminate burdens on various stakeholders in ETASU enforcement, and place ETASU enforcement in an early and more appropriate place in a patient care process. This may give prescribers and patients the opportunity to meet the safety requirements first, reducing unnecessary activity and potential rework. In addition, the eRx-based ETASU enforcement systems and methods may allow for a safe and effective way for prescriber-based REMS activities to be integrated into their various workflows. This may reduce burden, improve access, and foster better compliance and accuracy.

By incorporating an encrypted REMS Dispense Authorization (RDA) into eRxs, an eRx router may validate various elements of the eRx against encrypted data elements and thereby verify that any ETASUs required by a REMS for a prescribed drug have been complied with. As a result, only validated eRx are passed from the eRx router to pharmacies for dispensing, reducing manual intervention to confirm compliance. Information necessary to perform validation may be communicated to the eRx router by a Trusted Central RDA Authority (TCRA), and may include decryption keys, prescriber authorization data, and appropriate validation check algorithms.

In an embodiment, an electronic prescription router may receive an electronic prescription including an encrypted RDA portion. The electronic prescription router may determine that a REMS is in place for a drug associated with the electronic prescription, and decrypt the encrypted RDA portion of the electronic prescription using a REMS private key. The electronic prescription router may then validate a plurality of decrypted elements of the encrypted RDA portion of the electronic prescription, and after successful validation may communicate the validated electronic prescription from the electronic prescription router to a pharmacy system.

In some embodiments, there may be a TCRA, which may act as a single, trusted, central authority that is responsible for all RDA's that are issued for REMS associated with an REMS Administrator. The TCRA may coordinate encryption keys for RDAs for different REMS between originators and an eRx router. The TCRA may also coordinate certification of originators so that originators may be authorized to generate encrypted RDAs without per prescription interaction with the TCRA or a REMS Administrator.

In some embodiments, a REMS Administrator may provide a web interface for a healthcare provider to generate electronic prescriptions which incorporate encrypted RDAs and submit those prescriptions to an eRx router.

BRIEF DESCRIPTION OF THE DRAWINGS

A more detailed understanding may be had from the following description, presented by way of example in conjunction with the accompanying drawings, wherein:

FIG. 8 depicts pseudocode for one embodiment of a check algorithm for an eRx router to validate a received eRx with an encrypted RDA, in accordance with the present systems and methods.

DETAILED DESCRIPTION

Figure 1:
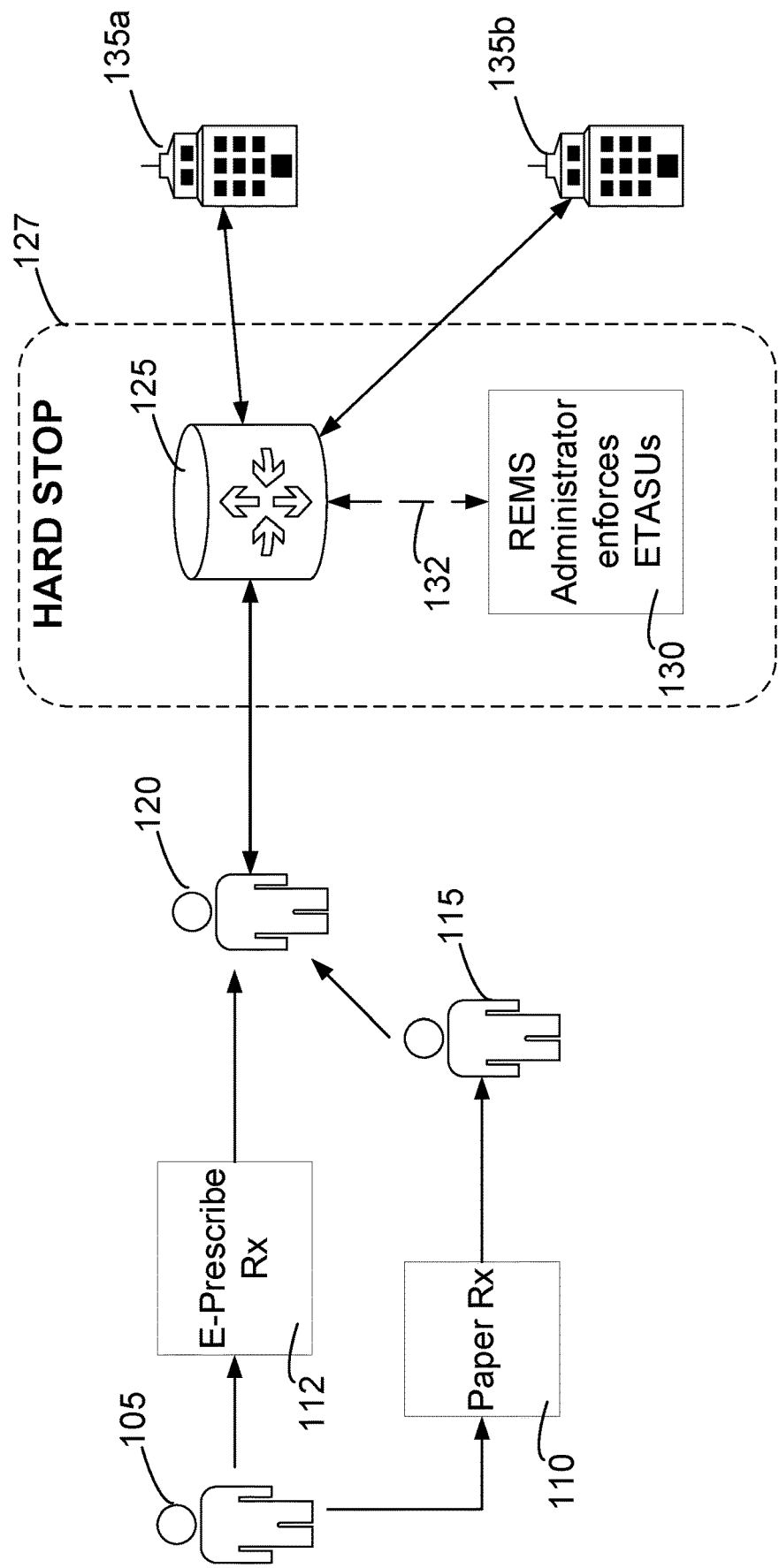
FIG. 1 depicts an embodiment of prior art payment based ETASU enforcement.

A detailed description of illustrative embodiments will now be provided with reference to the various Figures. Although this description provides detailed examples of possible implementations, it should be noted that the provided details are intended to be by way of example and in no way limit the scope of the application.

Note that various hardware elements of one or more of the described embodiments are referred to as "modules" that carry out (i.e., perform, execute, and the like) various functions that are described herein in connection with the respective modules. As used herein, a module includes hardware (e.g., one or more processors, one or more microprocessors, one or more microcontrollers, one or more microchips, one or more application-specific integrated circuits (ASICs), one or more field programmable gate arrays (FPGAs), one or more memory devices) deemed suitable by those of skill in the relevant art for a given implementation. Each described module may also include instructions executable for carrying out the one or more functions described as being carried out by the respective module, and it is noted that those instructions could take the form of or include hardware (i.e., hardwired) instructions, firmware instructions, software instructions, and/or the like, and may be stored in any suitable non-transitory computer-readable medium or media, such as commonly referred to as RAM, ROM, etc.

As discussed herein, an Originating System may be an electronic health record, practice management system, eRx platform, REMS implementation system, or other system that originates an eRx transaction. As discussed herein, an eRx Router may be an entity, often described as a health network, which acts as an intermediary connecting and facilitating the eRx transactions between the many Originating Systems to and from the many Participating Pharmacies. An example may be a system operated, for example, by Surescripts, or the like. As discussed herein, a Switch may be an entity that acts as an intermediary connecting and facilitating financial transactions between Pharmacies and Payers, e.g., health insurance and benefit management companies. As discussed herein, a Participating Pharmacy is a pharmacy that can receive and transmit eRx transactions, and is associated as an endpoint of an eRx network.

E-Prescription (eRx) Based ETASU Enforcement eRx-based ETASU enforcement is a superior Hard Stop implementation for REMS. It maintains and exceeds the benefits of the existing payment based ETASU enforcement approaches. eRx-based ETASU enforcement fits into the normal workflow of prescribers and, like its predecessor, does not rely on human manual intervention. It is superior to the current payment based Hard Stop because it places the enforcement of the ETASU at an earlier and more appropriate intersection point in the healthcare delivery process. The ETASU enforcement is upfront, immediately after, or in some cases simultaneously with the prescriber and patient interaction, and before the patient would attempt to fill a prescription. By incorporating an encrypted REMS Dispense Authorization (RDA) into eRxs, an eRx router may validate various elements of the eRx against encrypted data elements and thereby verify that any ETASUs required by a REMS for a prescribed drug have been complied with. As a result, only validated eRx are passed from the eRx router to pharmacies for dispensing, reducing manual intervention to confirm compliance. An embodiment of a eRx-based ETASU enforcement method is illustrated in FIG. 2.

Figure 2:
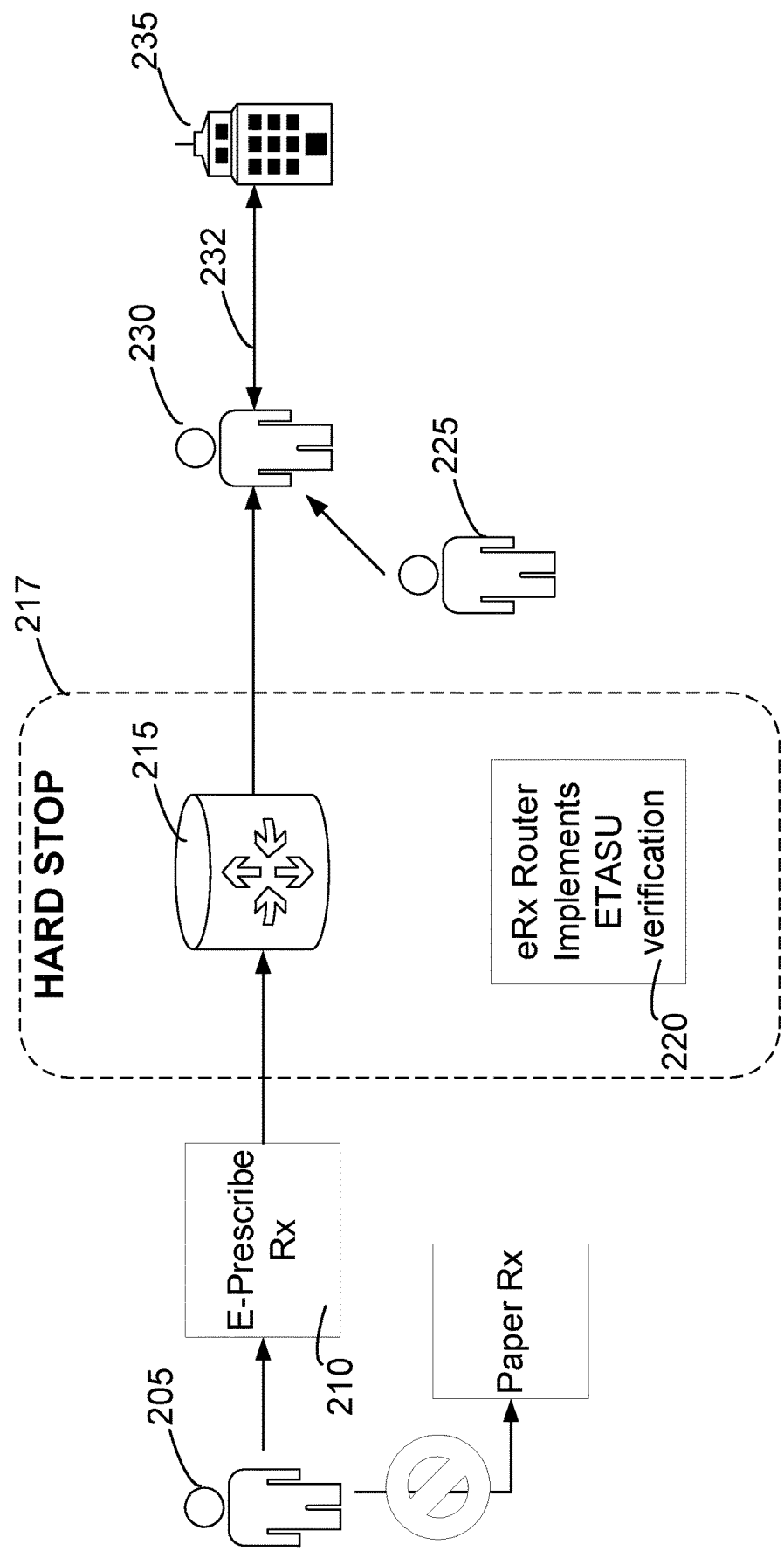
FIG. 2 depicts an embodiment of eRx-based ETASU enforcement, in accordance with the present systems and methods.

As shown in FIG. 2, the herein disclosed REMS enforcement implementation utilizes several major distinctions from current REMS implementations. These distinctions include:

ETASUs are enforced earlier and at a more appropriate intersection point within the patient care process.

eRx are mandated for use, in line with some public health goals.

Current responsibilities of pharmacies may be reduced or eliminated entirely.

Electronic health records, practice management systems, and other services may be able to participate in the REMS implementations.

The systems and methods set forth herein may reduce stakeholder burdens for prescribers, patients, and pharmacies.

In an embodiment of the eRx-based REMS enforcement implementation disclosed herein, as illustrated in the diagram of FIG. 2, a healthcare provider (e.g., doctor) (205) may e-prescribe an eRx (210) for a patient (225). In the embodiments set forth herein, paper prescriptions are no longer used, as the eRx processing steps permits certification and validation of REMS compliance. Once the eRx (210) is generated, it may be communicated through an eRx network to an eRx router (215), where a Hard Stop (217) may be implemented. Either through communication with an external entity or through information available at the eRx router, the eRx may be evaluated and ETASU compliance verified and/or validated (220). With the Hard Stop (217) successfully executed, the eRx may be forwarded from the eRx router (215) to a pharmacy (or equivalent system) (230), who may then dispense the prescription to the patient (225) without further need to perform any REMS related steps. This is because REMS compliance is verified before the eRx is passed to the pharmacist or pharmacy (230). In contrast to the existing REMS implementations, the pharmacy only needs to coordinate (232) with a payer (235) for insurance purposes, and does not implement a Hard Stop that may negatively impact the ability of a patient to receive their prescription.

REMS Administrator.

eRx-based ETASU enforcement starts with the REMS Administrator. REMS Administrators may retain all of their traditional responsibilities, and ultimately the responsibility of meeting the requirements of FDA mandated REMS, and especially the included ETASUs. In some embodiments, an implementation may include a call center for live support, a web site for stakeholders to perform their various ETASU related actions (e.g., enter lab results, record counseling, retrieve RDAs), etc. The REMS Administrator system may also be responsible for storing data supporting the operations and ETASU enforcement, and production of any assessment reports.

In addition to these existing REMS functions, the REMS Administrator may take on several new responsibilities. One of these new roles is for the REMS Administrator to act as a Trusted Central RDA Authority (TCRA). The TCRA is a single, trusted, central authority that is responsible for all RDA's that are issued for the REMS associated with the REMS Administrator. This may include RDAs issued from the REMS implementation system and from Federated RDA Originators (FROs).

In some embodiments, the TCRA may be a module of a REMS Administrator system that is in communication with an eRx network. In some embodiments, the TCRA may be a module of an eRx network system (e.g., eRx router).

The TCRA may be responsible for all RDAs that are issued for a given REMS. This includes RDAs issued from the REMS Administrator system and from FROs.

The TCRA may provide an eRx router with a list of drugs, via their unique identifiers, for inclusion in the ETASU enforcement protocols. The TCRA may also provide the eRx router with any required information and/or processing logic to validate RDAs.

The TCRA may also collect periodic data from the eRx router for both REMS assessment reporting and compliance monitoring purposes, including but not limited to: the number of RDAs intercepted, rejected, approved, and filled. Such reporting is discussed more fully below in relation to FIG. 5.

Another new role of the REMS Administrator may be to provide a REMS website with e-prescribing capabilities. For example, the REMS Administrator may enhance a typical website portion of an implementation system to include e-prescribing capabilities. This may allow prescribers to document and take actions necessary for the ETASUs, and initiate the patient prescription with a valid RDA from one central place. In addition, this may allow for participation of prescribers who have not yet implemented their own e-prescribing solutions or systems. In some embodiments, this web-based e-prescribing capability may be provided by the REMS Administrator in addition to functions based in existing eRx networks and their subscribers. Such web interfaces are discussed more fully below.

The REMS Administrator may also take on a role to create and administer a certification process for FROs, which may, for example, include Electronic Health Records (EHRs), practice management systems, e-prescribing platforms, and other healthcare systems. The certification process may ensure that the FROs: implement sufficient enforcement of the ETASUs; meet the regulatory requirements of a validated system; can issue a valid encrypted RDA; and can provide the resulting data for assessment reporting and compliance monitoring. The process of certification of FROs is discussed more fully below in relation to FIG. 4.

The FROs may be required to enroll with and be certified by the REMS Administrator. A FRO may enforce the REMS' ETASUs, issue e-prescriptions with valid encrypted RDAs, and submit data to the REMS Administrator for monitoring compliance and REMS assessment reporting. The FRO may either be provided any necessary logic and rules from the REMS Administrator system for generating encrypted RDAs, or may interface with the REMS Administrator to fulfill all requirements. The ability for FROs to participate in the REMS allows for the REMS to be appropriately implemented within the various workflows utilized by prescribers. As an example, a regional health network may have a centralized EHRs/practice management system that is capable of sending eRxs. For drugs under a REMS utilizing this model, the regional health network may have their system certified, after which HCPs within the network may write prescriptions for this drug within their normal course of practice.

Generally, an eRx router may select eRxs crossing its network if the identifier of a drug being prescribed is covered by a REMS implementing this model. The eRx router may then validate an encrypted RDA to ensure that the REMS' ETASUs have been met, and that the prescription and RDA are not expired. If this validation is successful the eRx may be passed through to the intended pharmacy or other endpoint of the eRx network that can receive prescriptions. If this validation is unsuccessful the eRx may be returned to the originator, in some cases with a rejection message.

It should be noted that in some embodiments, the eRx network and a pharmacy network may be integrated with one another. For example, an eRx router may be a component of a pharmacy network, where a pharmacy system may play the dual role of a pharmacy and an eRx router. In some cases, an integrated system may be present at a single pharmacy location, while in other cases an eRx router component of a pharmacy network may act as an eRx router for various locations of a pharmacy chain.

Due to the efficiency of the herein disclosed systems and methods for REMS implementation, some of the classic components of typical REMS are no longer required. In existing REMS, the pharmacy is the intersection point in the healthcare delivery process where ETASU enforcement and Hard Stops are implemented. This requires pharmacy management system updates, payment switch agreements, pharmacist REMS enrollment, training, attestations, and potentially more.

Using the systems and methods herein disclosed, a prescription is checked for REMS compliance before it arrives at the pharmacy. Therefore, the pharmacy, by receiving the eRx, may assume it is authorized by the REMS. There is no special handling required. Pharmacists may, however, need to be advised that paper prescriptions are not permitted for enrolled REMS drugs. This may be enforced, for example, as an ETASU via the prescriber enrollment and attestation.

Figure 3:
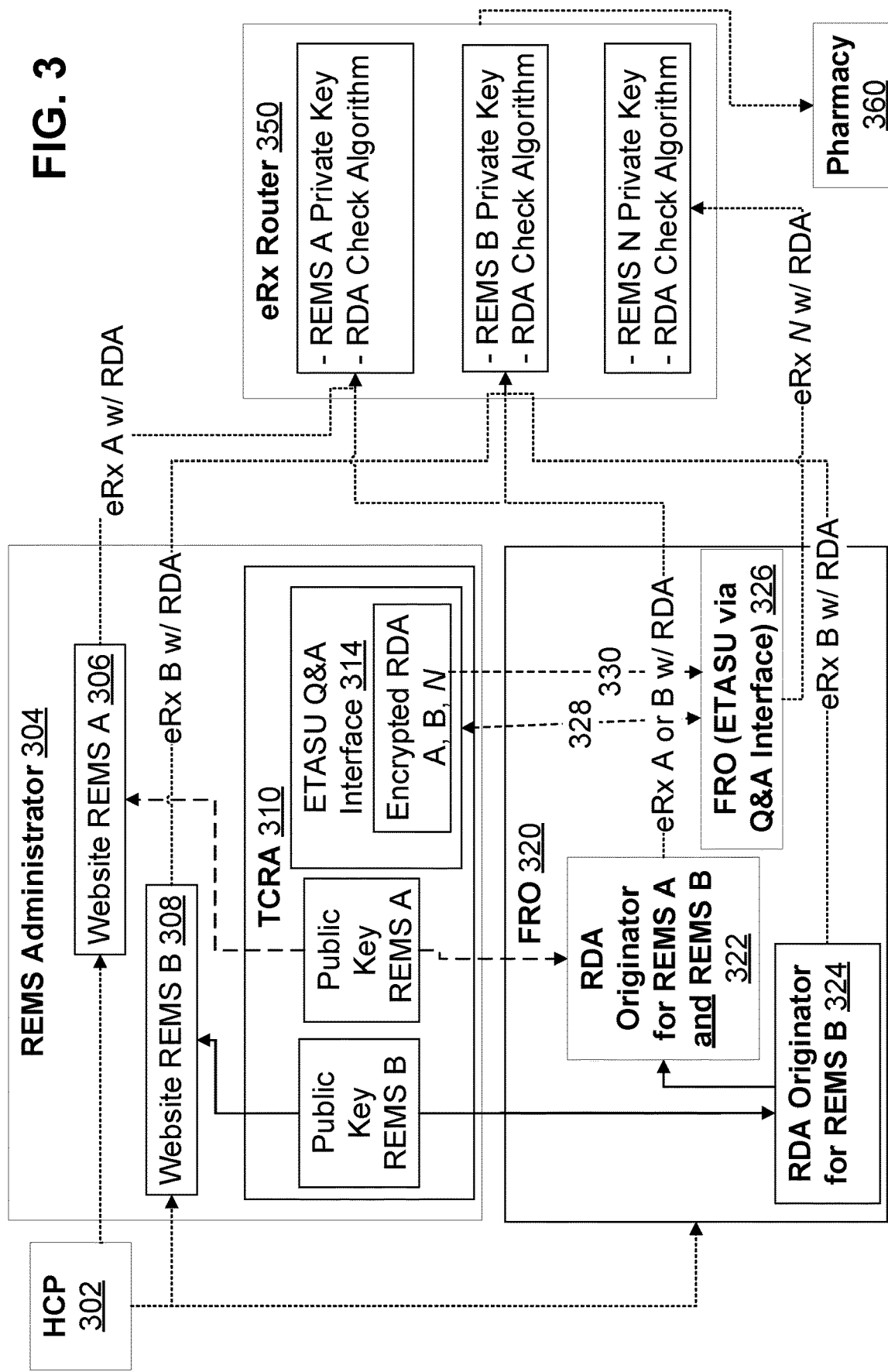
FIG. 3 illustrates a data flow diagram for one embodiment of processing an eRx and RDA, in accordance with the present systems and methods.

FIG. 3 illustrates a data flow diagram for one embodiment of processing an eRx and RDA, according to the present systems and methods. A healthcare provider (HCP) 302 may have a number of options for generating an eRx for a patient. In some cases, the HCP may use a web interface provided by a REMS Administrator 304 to prepare an eRx with an encrypted RDA. For example, the HCP 302 may use a website for a drug associated with a REMS A (306) to generate the eRx. The web interface 306 for REMS A may prompt the HCP 302 to confirm ETASU compliance and/or input relevant information for the eRx, and based on such HCP inputs may, for example in communication with a TCRA 310, retrieve an encryption key (such as a REMS A public key) and generated an eRx with an encrypted RDA (i.e., eRx A w/RDA). This generated eRx with encrypted RDA may then be communicated to an eRx router 350. The HCP may similarly use a REMS B web interface 308 to generate an eRx with an encrypted RDA for a second drug.

In some cases, the HCP 302 may be associated with a FRO 320, which has been certified or otherwise enabled by the TCRA to generate encrypted RDAs and verify ETASU compliance. The HCP 302 may interact with, for example, an electronic health records system associated with the FRO 320 to submit an eRx request for a patient. The FRO 320 may operate one or more RDA originator or generation modules 322, 324. In some cases, the RDA origination modules may be configured for a single REMS (e.g., module 324), and in some embodiments the RDA origination modules may be configured for multiple REMS (e.g., module 322), associated either with the same or different drugs. In some embodiments, the FRO 320 may not be certified to generate an encrypted RDA for a given drug associated with a REMS, and may have a module 326 configured to communicate with a TCRA interface 314, such as an ETASU Q&A interface, in order to obtain an encrypted RDA. In some embodiments, this may comprise queries and responses 328 between the FRO module 326 and the TCRA interface 314, which if successfully completed may cause the TCRA interface 314 to communicate an encrypted RDA 330 to the FRO module 326 for the given drug. The FRO module 326 may then communicate an eRx with the received encrypted RDA to an eRx router 350.

The eRx router 350 may have one or more modules for evaluating received eRxs. In some embodiments, there may be a separate module for each REMS, and in other embodiments a given module may evaluate eRxs associated with any of a plurality of REMS. Generally, received eRxs that are associated with a REMS will be decrypted (such as with a REMS private key) and validation of the decrypted RDA attempted (such as with an RDA check algorithm). If a given eRx with an encrypted RDA is successfully validated, it may be passed to a pharmacy 360 (or other endpoint of the eRx network that can receive prescriptions).

Because the systems and methods herein embed the ETASU Hard Stop into the eRx routing, this may require the prohibition of paper prescriptions for the drugs covered under this REMS model. While this is a departure from historic implementations, the impact may be relatively small. First, the adoption of e-prescribing as of 2015 is greater than 75%. In addition, a REMS Administrator website implementation may have e-prescribing capabilities, enabling prescribers to participate and comply with the REMS while only requiring web browser access.

Figure 4:
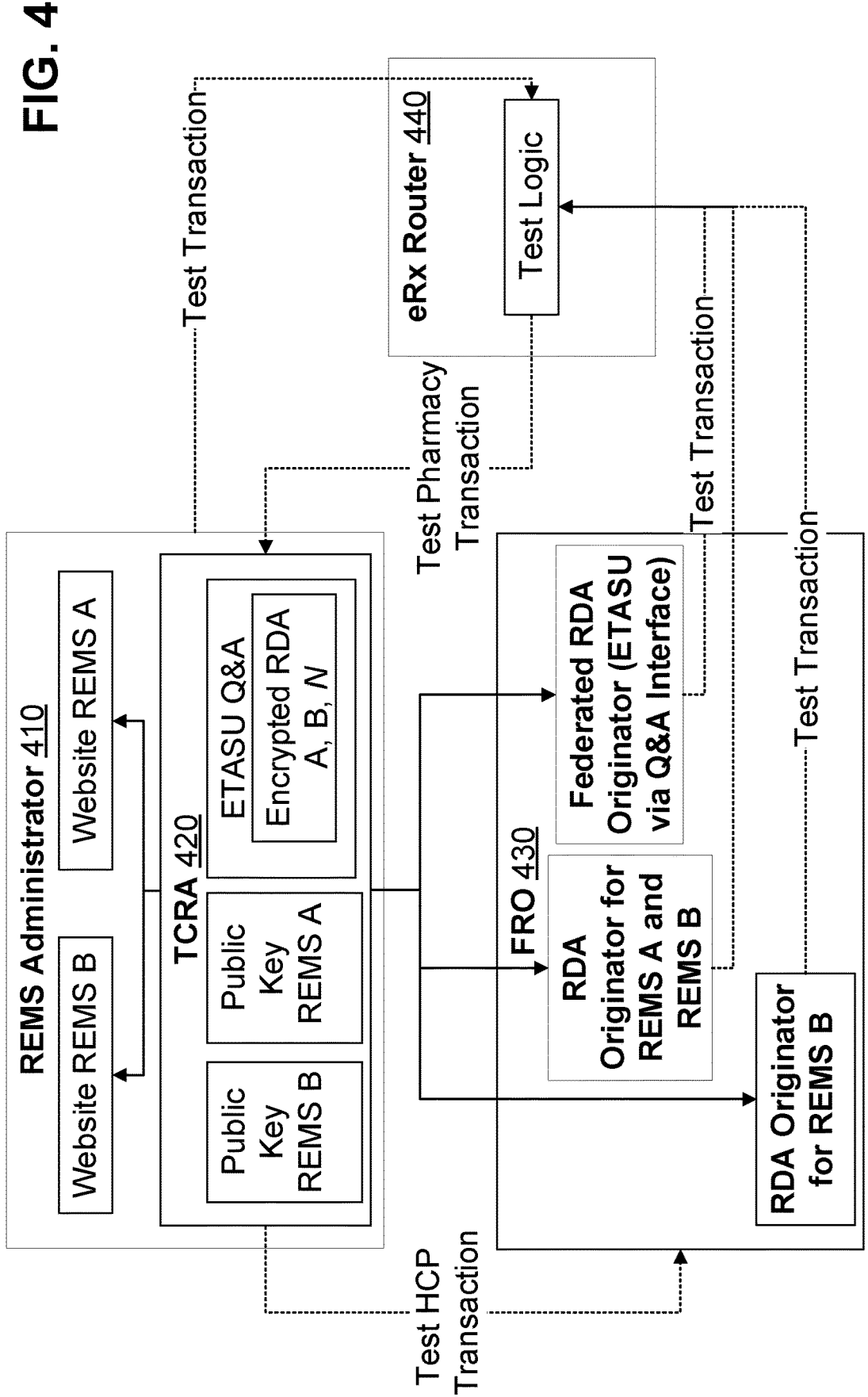
FIG. 4 illustrates an embodiment of a certification process for a Federated RDA Originator by a REMS Administrator, in accordance with the present systems and methods.

An embodiment of a certification process for a FRO 430 by a REMS Administrator 410 is illustrated in FIG. 4. In some embodiments, certification may include verifying that the Originators meet ETASU, Regulated, Technical, and Standards Requirements per REMS. It may also include communicating relevant Public Keys and Check Algorithms to Originators.

Once certification has been authorized for a given FRO 430 for a given REMS, and certification (and relevant information for generating encrypted RDAs) communicated to the FRO and/or FRO modules, test transactions may be carried out to verify the proper operation of the various interconnected systems. For example, a test HCP transaction for one or more REMS may be communicated from the TCRA 420 to the FRO 430. The appropriate FRO modules may process the test HCP transaction(s) to generate test eRxs with encrypted RDAs, and transmit these test eRxs to the eRx router 440. The eRx router 440 may carry out a test logic on the transaction, and communicate a test pharmacy transaction back to the TCRA 420 for verification of proper operation of the RDA methodologies. In some embodiments, the REMS Administrator 410 may communicate a test transaction (for example, from a REMS web interface) to the eRx router 440, which may operate a test logic and communicate a test pharmacy transaction back to the TCRA 420 for verification of proper operation.

Figure 5:
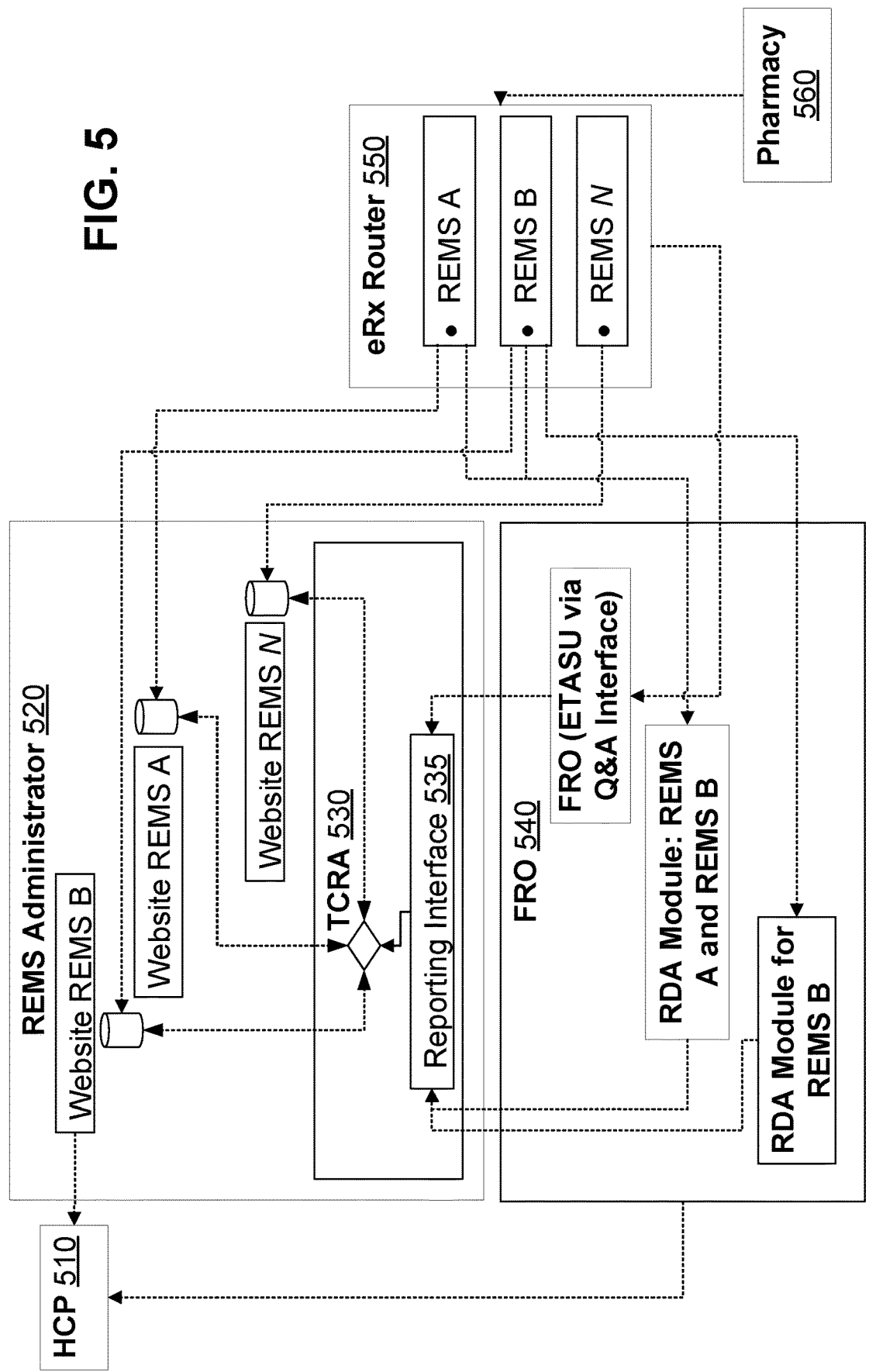
FIG. 5 illustrates one embodiment of a reporting process for REMS monitoring, in accordance with the present systems and methods.

FIG. 5 illustrates one embodiment of a reporting process for REMS monitoring and the like. In some embodiments, a pharmacy 560 may report to an eRx router 550 that a given eRx was filled. The eRx router 550 may process such reports on a per REMS basis (or any other appropriate organizational approach), and report prescription fill information back to the prescription source, either an FRO 540 or web interface operated by a REMS Administrator 520. In the case of an FRO 540, the relevant RDA module may receive the prescription transaction information from the eRx router 550, and may periodically transmit the transaction information back to the TCRA 530, such as a reporting interface 535. In some embodiments, the FRO 540 may also report prescription transaction information back to the prescribing HCP 510. In the case of REMS Administrator operated web interfaces, the interfaces may receive the prescription transaction information from the eRx router 550, and store the information locally and/or communicate the prescription transaction information to the TCRA 530. In some cases, the web interfaces (and/or the TCRA) may report the prescription transaction information back to the originating HCP 510. After reporting, the relevant REMS Administrator has received prescription transaction information and may perform a REMS assessment as necessary, such as to periodically produce a report of data and analysis for the FDA which may be used to determine the quality and effectiveness of the REMS.

In an embodiment, enforcement of ETASUs in relation to electronic prescriptions may be carried out by or in connection with an eRx router. For example, an eRx router may have sufficient capabilities to evaluate encrypted RDAs associated with eRx as received. In other embodiments, an eRx router may communicate with a TCRA on a periodic or per-eRx basis to evaluate encrypted RDAs.

While the discussion herein references encrypted and non-encrypted portions of communications between entities, it will be understood to those of skill in the art that such communications may be additionally protected in transit, and the such references are meant in relation to the encrypted RDA elements of the systems and methods set forth herein. For example, an eRx from a FRO or other healthcare provider may be encrypted for communication to an eRx router, without changing the underlying operation of the present systems and methods. Generally, for the purposes of the present disclosure it is presumed that each entity is able to securely transmit and receive messages and other information.

In one embodiment, an eRx router may receive an eRx, which includes an encrypted RDA portion. As noted, the RDA traditionally has been a unique number or code that is provided to a pharmacy that represents an authorization by the REMS Administrator for the patient to receive the drug at the time of the inquiry.

Based on, for example, a drug ID associated with the eRx, the eRx router may determine that there is at least one REMS in place for the drug associated with the eRx. In some embodiments, the drug ID may be the NDC code, a product name, or any comparable product identifier.

If there is no REMS in place for the particular drug being prescribed, the eRx router may simply process the eRx as usual, and communicate the eRx to a pharmacy system, or other eRx network endpoint capable of receiving a prescription.

With the appropriate REMS identified, the eRx router may retrieve from memory, look up, or otherwise obtain a decryption key in order to decrypt the encrypted RDA portion of the eRx. In one embodiment, the decryption key may be a REMS private key associated with the given drug ID. In some embodiments, the decryption key may be communicated to the eRx router at some prior time by a TCRA. In some embodiments, the decryption key may be communicated to the eRx router by a TCRA in response to a request from the eRx router during processing of an eRx. In some embodiments, the decryption key may be generated and maintained by the eRx router, without an external communication necessary to receive the key.

In some instances, the eRx router may fail to properly decrypt the encrypted RDA portion of the eRx. In such instances, the eRx router may report, for example, an RDA encryption error to the eRx source (e.g., FRO, TCRA, healthcare provider, etc.).

If the encrypted RDA portion of the eRx is properly decrypted, the eRx router may attempt to validate a plurality of elements from the decrypted RDA portion. In one embodiment, the validation may comprise a check algorithm, or the like.

In some embodiments, the validation may comprise comparing information from the eRx with information from the decrypted RDA portion of the eRx. For example, the eRx router may compare a patient identifier, a prescriber identifier, an eRx network identifier, an NDC code, an effective eRx date span (e.g., time window in which eRx may be filled), or the like from the eRx with entries for the same that were present in the encrypted RDA and have been decrypted.

In some embodiments, the validation may comprise comparing information from the decrypted RDA portion of the eRx with information stored at or otherwise accessible to the eRx router. For example, a set or list of ID pairs may be stored at or accessible to the eRx router, such as a list of FRO identifiers and eRx network identifiers. In one embodiment, the eRx router may attempt to match an FRO identifier and eRx network identifier from the decrypted RDA portion with an ID pair from a list of approved originators (or the like). In some embodiments, the list of ID pairs may be provided periodically to the eRx router by a TCRA, or in some embodiments may be provided responsive to a request from the eRx router. In some embodiments, if the pair of FRO and network identifiers (or some other combination of identifiers) from the RDA portion do not match records accessible to the eRx router, the eRx may be rejected.

In some embodiments, various other combinations of elements may be attempted to be validated, either in addition or alternative to ID pairs. For example, validation may compare a patient identifier from the decrypted RDA with a patient identifier from the eRx. Validation may compare a prescriber identifier from the decrypted RDA with a prescriber identifier from the eRx. Validation may compare an effective prescription date range from the decrypted RDA with an effective prescription date range from the eRx.

In some embodiments, if one or more of the plurality of decrypted elements of the encrypted RDA portion of the eRx cannot be validated, the eRx router may communicate a rejection message to a prescriber system. The rejection may also be recorded at the eRx router, in association with relevant information regarding the reasons the eRx was rejected.

Once all (or all relevant) decrypted elements of the encrypted RDA portion of the eRx have been validated, the eRx router may communicate the validated eRx from the router to a pharmacy system (or any endpoint of an eRx network that can receive prescriptions).

In some embodiments, the eRx router may report eRx processing data from the router to a TCRA system (as partially discussed in relation to FIG. 5 above). Such reporting may occur periodically (e.g., quarterly, monthly, weekly, etc.), on an as requested basis, with each processed eRx, or the like. Such reported information may comprise the number of processed eRxs for a given REMS, the number of rejected eRxs for a given REMS, number of eRxs received overall, and/or the like. In some embodiments, other information may also be reported by the eRx router. A TCRA may use reporting information received from the eRx router for REMS assessment reporting and compliance monitoring purposes.

Figure 6:
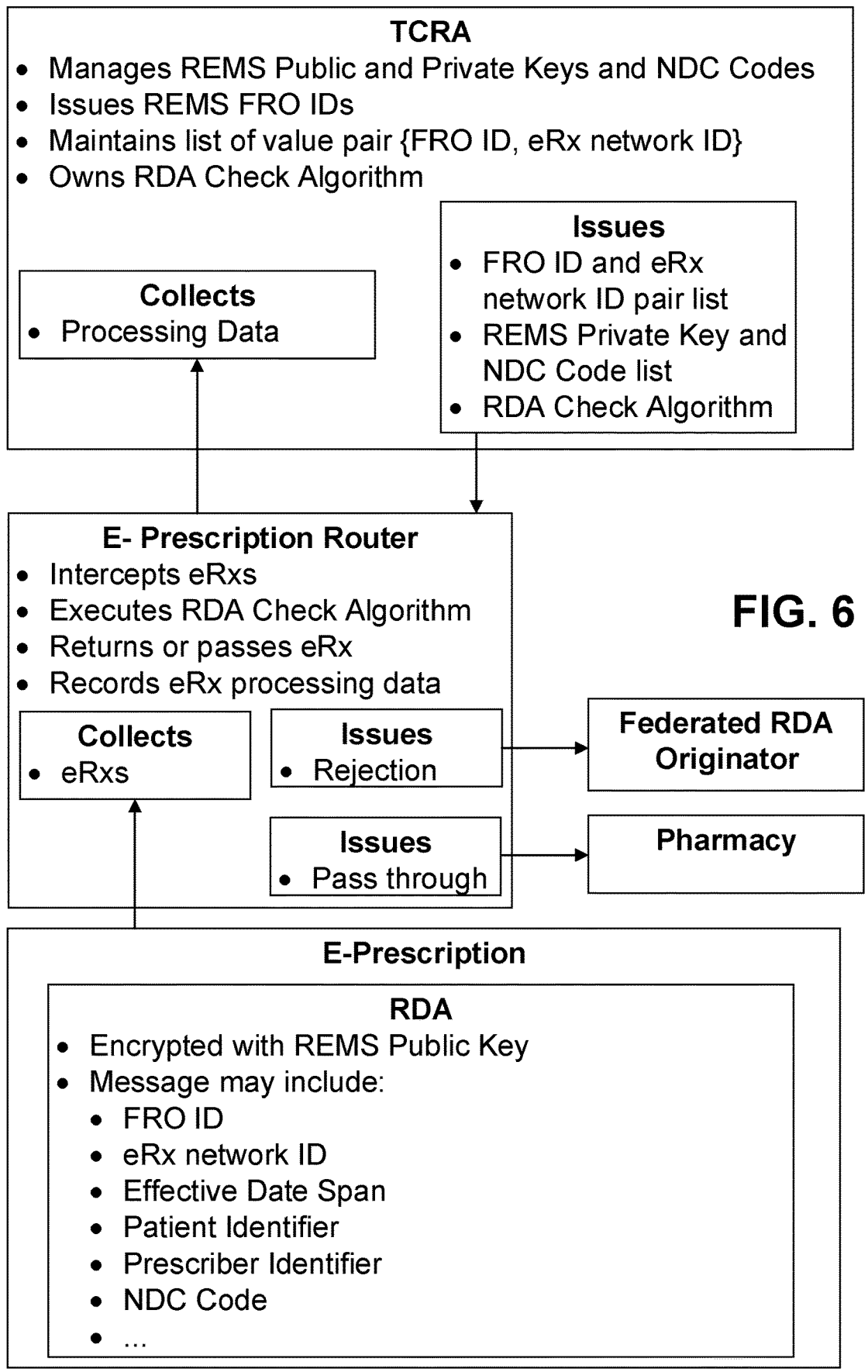
FIG. 6 illustrates a data flow diagram for one embodiment of an eRx router receiving and checking an eRx with an encrypted RDA, in accordance with the present systems and methods.
Figure 7:
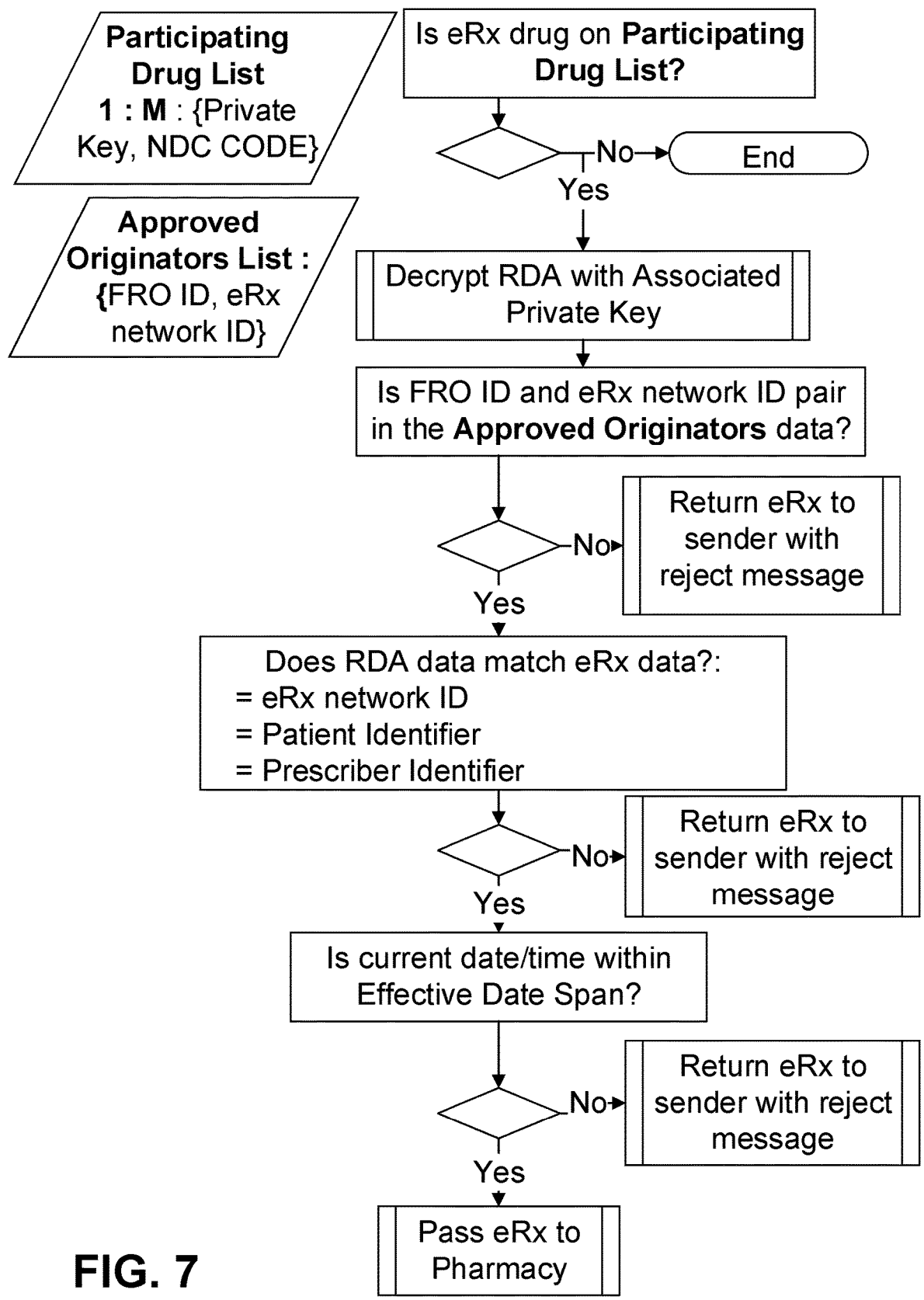
FIG. 7 illustrates a block diagram for one embodiment of an eRx router processing a received eRx with an encrypted RDA, in accordance with the present systems and methods.

A data flow diagram for one embodiment of an eRx router receiving and checking an eRx with an encrypted RDA is illustrated in FIG. 6. A block diagram for one embodiment of an eRx router processing a received eRx with an encrypted RDA is illustrated in FIG. 7. Pseudocode for one embodiment of a check algorithm for an eRx router to validate a received eRx with an encrypted RDA is illustrated in FIG. 8.

In an embodiment, a FRO may be authorized by a TCRA to generate an encrypted RDA for inclusion in an eRx that will be submitted to an eRx router. This certification/authorization process may be carried out at any time prior to the FRO generating an eRx with an encrypted RDA portion (see discussion related to FIG. 4).

Once the FRO has received sufficient information and/or certification from a TCRA (or other entity) to generate an encrypted RDA, at some time the FRO may receive an eRx request from a healthcare provider for a drug associated with one or more REMS. The FRO may determine any ETASUs associated with the one or more REMS for the given drug, and confirm compliance with those ETASUs. Generally, all ETASUs associated with the relevant REMS for a given drug must be complied with in order for the eRx request to be properly processed and an encrypted RDA generated for the eRx request. In some embodiments, confirming compliance may comprise evaluating electronic health records available at the FRO, requesting verification of compliance from one or more individual healthcare providers associated with the FRO (e.g., doctors, nurses, etc.), and/or the like.

With REMS compliance confirmed, the FRO may proceed to generate an encrypted RDA for the eRx request. In some embodiments, the RDA may be encrypted at least in part using a public key associated with the one or more REMS for the given drug. In some cases, this public key may have been previously provided to the FRO by the TCRA. In other embodiments, alternative encryption methodologies may be utilized, rather than public/private key pairs (e.g., asymmetric cryptography).

In some embodiments, the RDA which is encrypted may include various data elements. For example, in various embodiments, information encrypted in the RDA may include, but is not limited to: a FRO ID associated with the FRO (for example, as assigned by the TCRA); an eRx network ID associated with the FRO; an effective date span for the electronic prescription; a patient ID; a prescriber ID (e.g., doctor); a NDC code or other drug identifier; and/or the like.

With any ETASUs for one or more REMS associated with the prescription request satisfied, and the encrypted RDA generated, the FRO system may transmit an eRx including the generated encrypted RDA from the FRO to an electronic prescription router, for example a participating eRx router for an eRx network in which the FRO is a participant.

Figure 9:
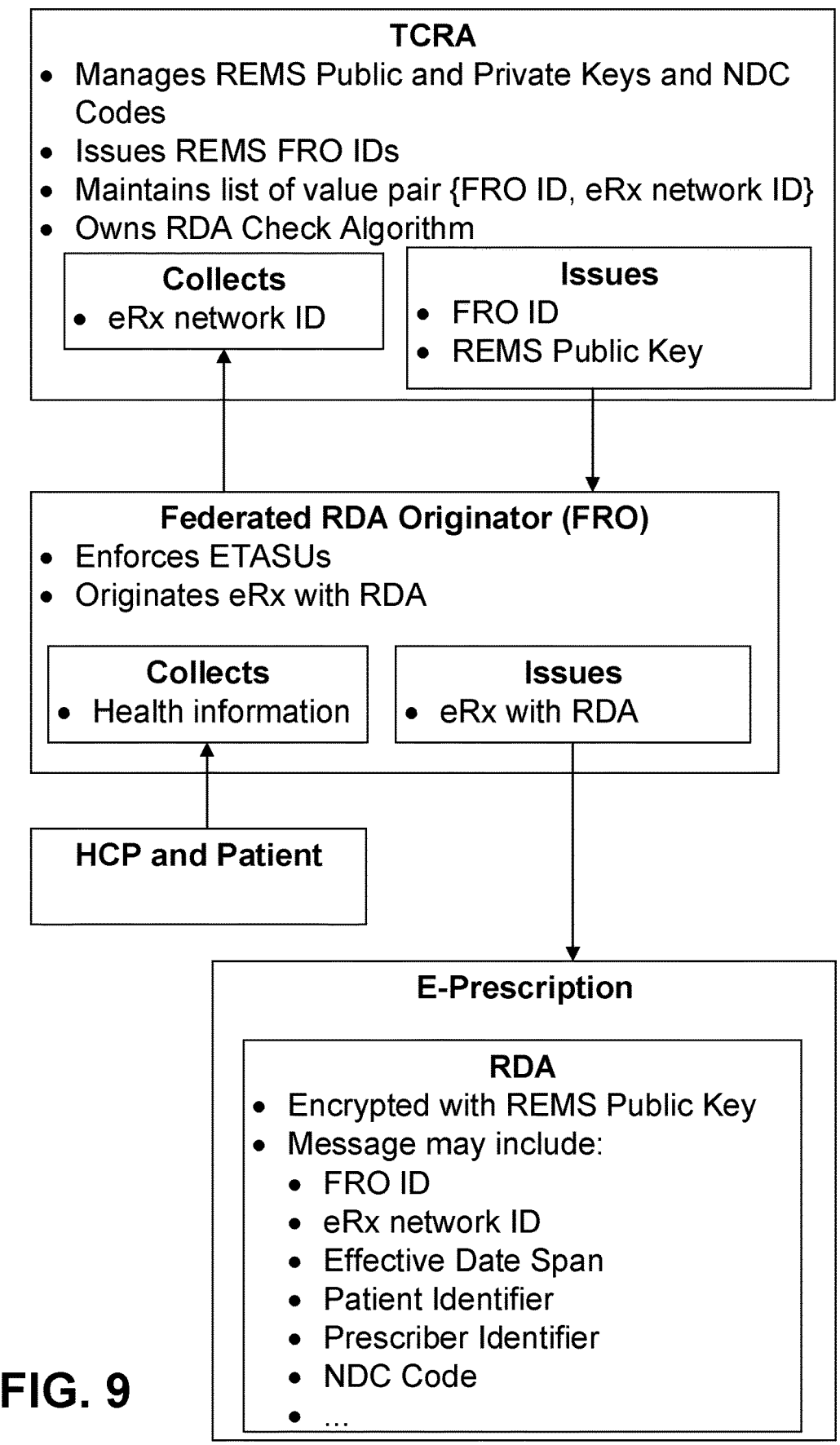
FIG. 9 illustrates a data flow diagram in one embodiment for generation of an eRx with an encrypted RDA by a FRO, in accordance with the present systems and methods.

An illustration of the data flow for generation of an eRx with an encrypted RDA by a FRO in one embodiment of the present systems and methods is set forth in FIG. 9. In the embodiment illustrated in FIG. 9, communications between the TCRA and FRO may occur at any time prior to the generation of an eRx with an encrypted RDA, or in some cases concurrent with eRx generation.

In an embodiment, a health system (or electronic healthcare records system, hospital system, or the like) may not be certified or otherwise authorized by a TCRA to generate encrypted RDAs for inclusion in eRxs. In such cases, the methods disclosed herein may be adapted to permit a TCRA (or other entity) to receive relevant information from the health system and return an encrypted RDA for inclusion in an eRx. Similar embodiments were previously discussed in relation to FRO modules and TCRA modules in FIG. 3.

Similar to where a health system or FRO is certified or authorized by a TCRA (or other entity) to generate an encrypted RDA, the health system may receive an eRx request from a healthcare provider for a drug associated with at least one REMS. The system may then confirm compliance with all ETASUs associated with the at least one REMS. In some embodiments, confirming compliance may comprise evaluating electronic health records available at the health system, requesting verification of compliance from one or more individual healthcare providers associated with the health system (e.g., the healthcare provider, doctors, nurses, etc.), and/or the like.

Once the system has confirmed compliance with any REMS associated with the given drug being prescribed, the system may communicate a plurality of data elements associated with the eRx request to a TCRA or TCRA system (or similar entity). These data elements may include, but are not limited to: a system ID associated with the health system (for example, as assigned by the TCRA); an e-prescribing network ID associated with the health system; an effective date span for the electronic prescription; a patient ID; a prescriber ID (e.g., doctor); a NDC code or other drug identifier; and/or the like. In some embodiments, while some data elements are communicated from the system to the TCRA, others may be available at the TCRA and not communicated from the system (e.g., a system RDA ID, an eRx network ID, etc.).

The TCRA may receive the plurality of data elements, and based on those elements (and possibly other data elements already available at the TCRA) generate an encrypted RDA for the eRx request. The encrypted RDA may be encrypted at least in part using a public key associated with the relevant REMS. In some embodiments, encrypted RDA may be encrypted using an entirely private key methodology, rather than a public key portion of an asymmetric cryptography methodology. The encrypted RDA may then be communicated back to the health system for inclusion in the eRx.

Once the encrypted RDA is received at the health system, it may be incorporated into the eRx request, and an eRx may be transmitted from the health system to an eRx router (or the like). The eRx may be based at least in part on the eRx request and include the received encrypted RDA.

In an embodiment, a TCRA may receive a request from a healthcare provider for an encrypted RDA for an eRx for a drug associated with a REMS. The TCRA may request confirmation from the healthcare provider of compliance with any ETASUs associated with the REMS. The TCRA may request and/or receive a plurality of data elements from the healthcare provider, and based at least in part on the plurality of received data elements may generate a RDA for the eRx. As previously noted, the plurality of data elements may include, but are not limited to: a healthcare provider ID associated with the health system (for example, as assigned by the TCRA); an e-prescribing network ID associated with the healthcare provider; an effective date span for the electronic prescription; a patient ID; a prescriber ID (e.g., doctor); a NDC code or other drug identifier; and/or the like. In some embodiments, the TCRA may also have access to one or more data elements which are not received from the healthcare provider (for example, one or more of the above listed data elements), which may be included in the generated RDA.

The TCRA may then encrypt the generated RDA, for example with a REMS public key associated with the REMS. In some embodiments, asymmetric cryptography methods may be used (e.g., public/private key pairs), while in other embodiments private keys alone may be used for encryption. For example, where the encrypted RDA is being communicated from the TCRA to a health system or healthcare provider for inclusion in an eRx, it may be appropriate for a private key known to the TCRA (and possibly shared with an eRx router) to be used rather than a public/private key scheme.

The encrypted RDA may be communicated from the TCRA back to the healthcare provider, for inclusion in an eRx.

In some embodiments, rather than a RDA being generated and then encrypted, the TCRA may directly generate the encrypted RDA.

In some embodiments, the TCRA may store, in association with a given REMS, a value pair associating a TCRA-assigned ID for a healthcare provider and an eRx network ID associated with the healthcare provider. In some embodiments, the eRx network ID may be received at the TCRA from the healthcare provider.

In an embodiment, a TCRA may itself provide an interface through which healthcare providers (e.g., doctors) who do not have eRx capabilities may submit eRxs to an eRx router. In some cases, healthcare providers may be required to register with the TCRA prior to submitting eRx requests.

At some point, a TCRA may receive a request from a healthcare provider for an eRx for a drug associated with a REMS. The TCRA determine any ETASUs that are associated with the REMS, and either request and/or receive confirmation of compliance with those ETASUs from the healthcare provider. The TCRA may, for example, request copies of electronic health records, request a healthcare provider affirmatively confirm compliance with the ETASUs (e.g., check yes boxes within an online interface, etc.), or the like.

With REMS compliance confirmed, the TCRA may generate, based at least in part on a plurality of data elements received from the healthcare provider, a RDA for the eRx. As previously noted, the plurality of data elements may include, but are not limited to: an effective date span for the electronic prescription; a patient ID; a prescriber ID (e.g., doctor); a NDC code or other drug identifier; and/or the like. In some embodiments, the TCRA may also have access to one or more data elements which are not received from the healthcare provider (for example, a healthcare provider RDA ID assigned by the TCRA and associated with the healthcare provider or an eRx network ID associated with the TCRA and/or the healthcare provider, one or more of the elements noted above, etc.), which may be included in the generated RDA.

The TCRA may then encrypt the generated RDA. In some embodiments, the generated RDA may be encrypted with a REMS public key associated with the REMS. In some embodiments, the generated RDA may be encrypted with a private key associated with the REMS, without the use of an asymmetric cryptography methodology. In some embodiments, rather than a RDA being generated and then encrypted, the TCRA may directly generate the encrypted RDA.

In some embodiments, the TCRA may store, in association with the REMS, a value pair associating a TCRA-assigned ID for the healthcare provider and an eRx network ID associated with the healthcare provider and/or the TCRA.

In accordance with some embodiments, there is a method, including: receiving, at an electronic prescription router (eRx-R), an electronic prescription including an encrypted REMS Dispense Authorization (RDA) portion; determining, based on a drug ID associated with the electronic prescription, that a REMS is in place for a drug associated with the electronic prescription; decrypting the encrypted RDA portion of the electronic prescription using a REMS private key associated with the drug ID; validating a plurality of decrypted elements of the encrypted RDA portion of the electronic prescription; and communicating the validated electronic prescription from the eRx-R to a pharmacy system. The method may include wherein validating the plurality of decrypted elements of the encrypted RDA portion of the electronic prescription comprises validating a decrypted federated RDA originator ID and a decrypted e-prescribing network ID pair with an ID pair stored at the eRx-R. The method may include wherein the ID pair is received at the eRx-R from a Trusted Central RDA Authority system at a prior time. The method may include wherein validating the plurality of decrypted elements of the encrypted RDA portion of the electronic prescription comprises validating a decrypted e-prescribing network ID with an unencrypted e-prescribing network ID associated with the electronic prescription. The method may include wherein validating the plurality of decrypted elements of the encrypted RDA portion of the electronic prescription comprises validating a decrypted patient ID with an unencrypted patient ID associated with the electronic prescription. The method may include wherein validating the plurality of decrypted elements of the encrypted RDA portion of the electronic prescription comprises validating a decrypted prescriber ID with an unencrypted prescriber ID associated with the electronic prescription. The method may include wherein validating the plurality of decrypted elements of the encrypted RDA portion of the electronic prescription comprises validating a decrypted effective date span with a current date. The method may further include wherein if at least one of the plurality of decrypted elements of the encrypted RDA portion of the electronic prescription cannot be validated, communicating a rejection message to a prescriber system. The method may further include reporting electronic prescription processing data from the eRx-R to a Trusted Central RDA Authority system.

In accordance with some embodiments, there is a method including: receiving, at a Federated RDA Originator (FRO), an electronic prescription request from a healthcare provider for a drug associated with a REMS; confirming, at the FRO, compliance with any ETASUs associated with said REMS; generating an encrypted RDA for the electronic prescription request, wherein the encrypted RDA is encrypted at least in part using a public key associated with said REMS; and transmitting an electronic prescription including the generated encrypted RDA from the FRO to an electronic prescription router. The method may include wherein the public key associated with said REMS is received at the FRO at a prior time. The method may include wherein at least one element of the encrypted RDA comprises a FRO ID associated with the FRO. The method may include wherein the FRO ID associated with the FRO is received at the FRO from a Trusted Central Authority at a prior time. The method may include wherein at least one element of the encrypted RDA comprises an e-prescribing network ID associated with the FRO. The method may include wherein at least one element of the encrypted RDA comprises an effective date span for the electronic prescription. The method may include wherein at least one element of the encrypted RDA comprises a patient ID. The method may include wherein at least one element of the encrypted RDA comprises a prescriber ID. The method may include wherein at least one element of the encrypted RDA comprises an NDC code.

In accordance with some embodiments, there is a method including: receiving, at an electronic healthcare system, an electronic prescription request from a healthcare provider for a drug associated with a REMS; confirming, at the electronic healthcare system, compliance with at least one ETASU associated with said REMS; communicating, from the electronic healthcare system to a Trusted Central RDA Authority (TCRA), a plurality of data elements associated with the electronic prescription request; receiving, from the TCRA, an encrypted RDA for the electronic prescription request; and transmitting, from the electronic healthcare system to an electronic prescription router, an electronic prescription based at least in part on the electronic prescription request and including the received encrypted RDA. The method may include wherein at least one element of the encrypted RDA comprises a TCRA-assigned ID associated with the electronic healthcare system. The method may include wherein at least one element of the encrypted RDA comprises an e-prescribing network ID associated with the electronic healthcare system. The method may include wherein at least one element of the encrypted RDA comprises an effective date span for the electronic prescription. The method may include wherein at least one element of the encrypted RDA comprises a patient ID. The method may include wherein at least one element of the encrypted RDA comprises a prescriber ID. The method may include wherein at least one element of the encrypted RDA comprises an NDC code.

In accordance with some embodiments, there is a method, including: receiving, at a Trusted Central RDA Authority (TCRA), a request from a healthcare provider for an encrypted RDA for an electronic prescription for a drug associated with a REMS; receiving, at the TCRA, confirmation from the healthcare provider of compliance with at least one ETASU associated with said REMS; generating, based at least in part on a plurality of data elements received from the healthcare provider, an encrypted RDA for the electronic prescription; and communicating the encrypted RDA from the TCRA to the healthcare provider. The method may include wherein at least one element of the encrypted RDA comprises an e-prescribing network ID associated with the healthcare provider. The method may include wherein at least one element of the encrypted RDA comprises an effective date span for the electronic prescription. The method may include wherein at least one element of the encrypted RDA comprises a patient ID. The method may include wherein at least one element of the encrypted RDA comprises a prescriber ID. The method may include wherein at least one element of the encrypted RDA comprises an NDC code. The method may further include storing at the TCRA, in association with said REMS, a value pair associating a TCRA-assigned ID for the healthcare provider and an e-prescribing network ID associated with the healthcare provider. The method may include wherein said e-prescribing network ID is received at the TCRA from the healthcare provider. The method may include wherein the encrypted RDA is encrypted at least in part using a public key associated with said REMS. The method may include wherein the encrypted RDA is encrypted at least in part using a private key associated with said REMS.

In accordance with some embodiments, there is a method, including: receiving, at a Trusted Central RDA Authority (TCRA), a request from a healthcare provider for an electronic prescription for a drug associated with a REMS; receiving, at the TCRA, confirmation from the healthcare provider of compliance with at least one ETASU associated with said REMS; generating, based at least in part on a plurality of data elements received from the healthcare provider, an encrypted RDA for the electronic prescription; and communicating an electronic prescription including the encrypted RDA from the TCRA to an electronic prescription router. The method may include wherein at least one element of the RDA comprises an e-prescribing network ID associated with the TCRA. The method may include wherein at least one element of the RDA comprises an effective date span for the electronic prescription. The method may include wherein at least one element of the RDA comprises a patient ID. The method may include wherein at least one element of the RDA comprises a prescriber ID. The method may include wherein at least one element of the RDA comprises an NDC code. The method may further include storing at the TCRA, in association with said REMS, a value pair associating a TCRA-assigned ID for the healthcare provider and an e-prescribing network ID associated with the TCRA. The method may include wherein the encrypted RDA is encrypted at least in part using a public key associated with said REMS. The method may include wherein the encrypted RDA is encrypted at least in part using a private key associated with said REMS.

In accordance with some embodiments, there is a system including a processor and a non-transitory storage medium storing instructions operative, when executed on the processor, to perform functions including: receiving, at an electronic prescription router (eRx-R), an electronic prescription including an encrypted REMS Dispense Authorization (RDA) portion; determining, based on a drug ID associated with the electronic prescription, that a REMS is in place for a drug associated with the electronic prescription; decrypting the encrypted RDA portion of the electronic prescription using a REMS private key associated with the drug ID; validating a plurality of decrypted elements of the encrypted RDA portion of the electronic prescription; and communicating the validated electronic prescription from the eRx-R to a pharmacy system.

In accordance with some embodiments, there is an electronic prescription router system including: a processor; a receiver; a transmitter; an electronic prescription evaluation module configured to validate a plurality of decrypted elements of an encrypted RDA portion of a received electronic prescription; and a non-transitory data storage medium. The system may further include a RDA decryption module configured to decrypt the encrypted RDA portion of the received electronic prescription. The system may include wherein a decryption key is received at the electronic prescription router system from a Trusted Central RDA Authority. The system may further include a reporting module configured to report electronic prescription processing data from the electronic prescription router to a Trusted Central RDA Authority system.

In accordance with some embodiments, there is a Trusted Central RDA Authority (TCRA) system including: a processor; a receiver; a transmitter; a certification/authorization module configured to certify and authorize third party systems to generate encrypted RDA portions for electronic prescriptions and communicate encryption credentials to said third party systems; and a non-transitory data storage medium. The system may further include a RDA decryption module configured to decrypt the encrypted RDA portion of an electronic prescription. The system may include wherein a decryption key is stored in the data storage medium. The system may further include a reporting module configured to receive electronic prescription processing data from external sources. The system may further include a RDA encryption module configured to generate an encrypted RDA portion for an electronic prescription. The system may further include an ETASU interface configured to confirm ETASU compliance for a given REMS for an electronic prescription being generated by a healthcare system which is not authorized to generate encrypted RDAs. The system may further include an electronic prescription evaluation module configured to validate a plurality of decrypted elements of an encrypted RDA portion of an electronic prescription.

In accordance with some embodiments, there is a federated RDA originator (FRO) system including: a processor; a receiver; a transmitter; a RDA encryption module configured to generate an encrypted RDA portion for an electronic prescription based on stored and received data and a RDA encryption key received from a Trusted Central RDA Authority system; and a non-transitory data storage medium. The system may further include a reporting module configured to report electronic prescription processing data from the FRO system to the Trusted Central RDA Authority system.

Figure 10:
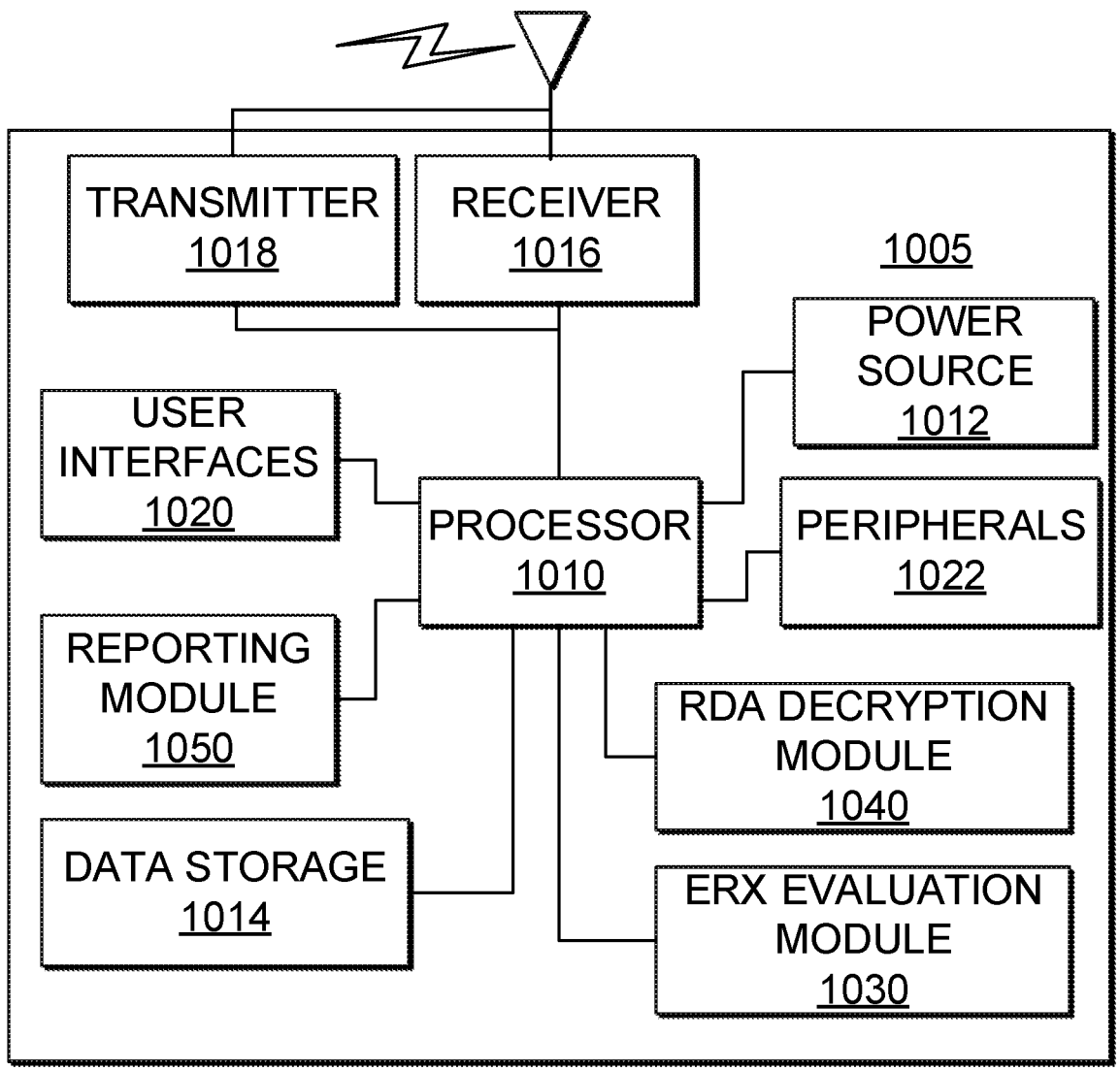
FIG. 10 illustrates an exemplary eRx router system that may be employed in some embodiments.

In an embodiment, as illustrated in FIG. 10, there may be a system for an eRx router. The eRx system 1005 may comprise a processor 1010, a power source 1012 (which may be any power source suitable for the system), a data storage 1014, a receiver module 1016, a transmitter module 1018, and an eRx evaluation module 1030. In some cases, the system may comprise a user interface 1020, such as a touchpad, a keyboard, a display, a speaker/microphone, and/or the like. In some cases, the system may comprise a decryption module 1040. In some cases, various peripherals 1022, as known to those of skill in the art, may be used with or incorporated into the system.

The transmitter module and receiver module may be configured to transmit and receive signals for the system. The signals may be received over wired (e.g., ethernet, etc.) or wireless (e.g., LTE, Wi-Fi, Bluetooth, etc.) connections. The data storage may be non-removable or removable, and may include random-access memory, read-only memory, a hard disk, flash memory, a secure digital memory card, or any other type of memory storage device.

In various embodiments, data or information received at or acted upon by a given module may either be retained at the given module or be accessible to the given module from a data storage of the system. For example, previously received ID pairs may be retained in the data storage, but be accessible by an eRx evaluation module.

In various embodiments, the transmit and receive modules may be combined into a single module, or remain as distinct modules.

The eRx evaluation module may be configured to perform the check evaluations for eRxs received at the eRx router, as previously discussed. In some cases, the module may communicate with a TCRA system to receive decryption credentials for one or more drugs, prescribers/prescriber systems, etc. Received eRxs may then have their encrypted RDAs decrypted by a RDA decryption module 1040 of the system, after which the RDA check evaluations may be conducted by the evaluation module. In some embodiments, there may be a check evaluation module for each REMS, while in other embodiments there may be a check evaluation module for a plurality of REMSs. In some embodiments, there may be a decryption module for each REMS, while in other embodiments there may be a decryption module for a plurality of REMSs. In some embodiments, a decryption module may be combined with a check evaluation module. In some embodiments, the decryption module may receive, either on demand or at some time prior to a decryption, decryption credentials from a TCRA or other system.

Once an eRx has been successfully checked by the eRx router system, the transmitter module may communicate the validated eRx to a pharmacy system.

The eRx router may also comprise a reporting module 1050, which may report prescription information back to a TCRA system (see FIG. 5 and related discussion).

Figure 11:
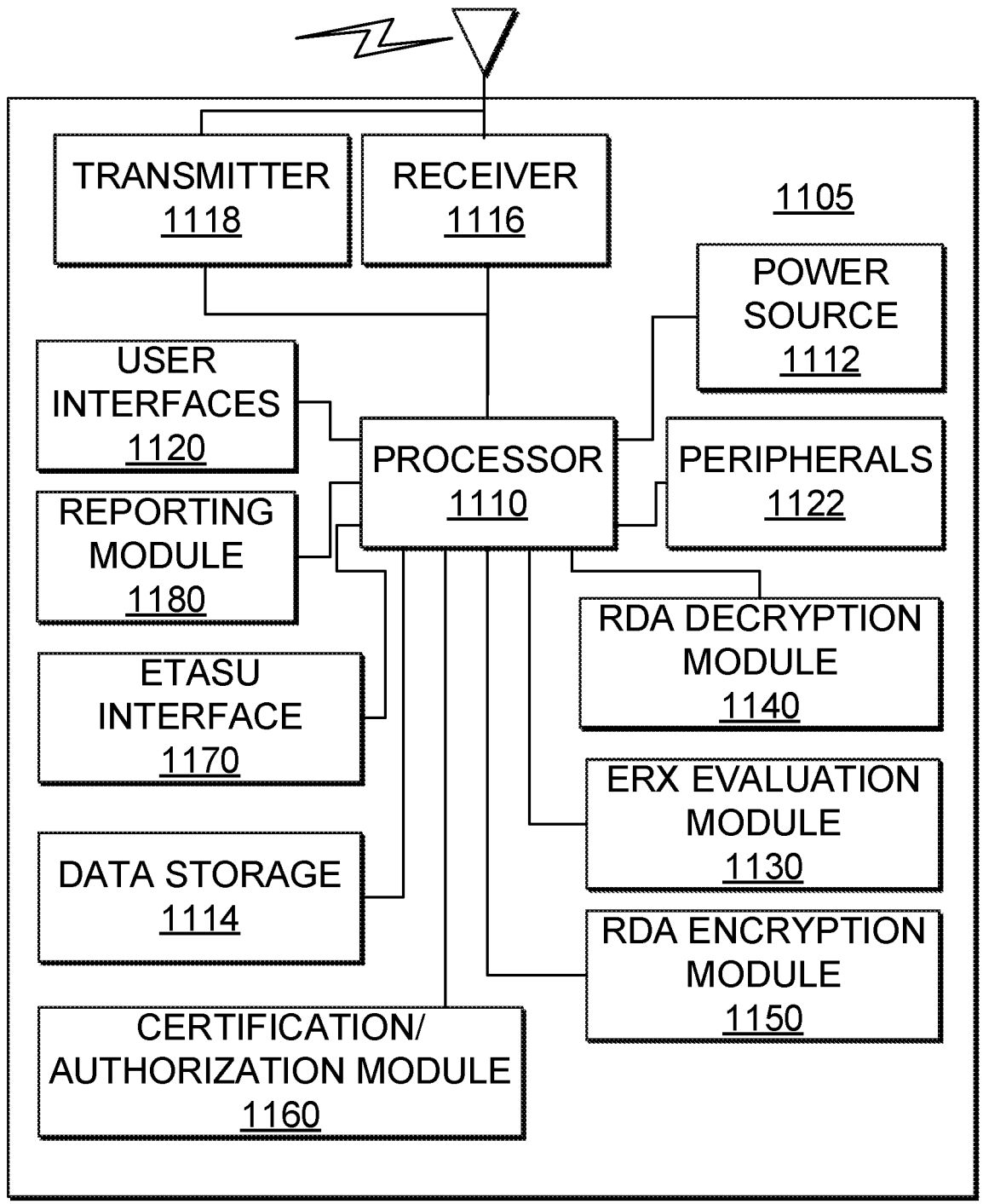
FIG. 11 illustrates an exemplary TCRA system that may be employed in some embodiments.

In some embodiments, as illustrated in FIG. 11, a TCRA system 1105 may comprise a processor 1110, a power source 1112 (which may be any power source suitable for the system), a data storage 1114, a receiver module 1116, and a transmitter module 1118. In some embodiments, the TCRA system may also comprise one or more of an eRx evaluation module 1130, a RDA decryption module 1140, a RDA encryption module 1150, and a certification/authorization module 1160. In some cases, the system may comprise a user interface 1120, such as a touchpad, a keyboard, a display, a speaker/microphone, and/or the like. In some cases, various peripherals 1122, as known to those of skill in the art, may be used with or incorporated into the system. The transmitter module and receiver module may be configured to transmit and receive signals for the system. The signals may be received over wired (e.g., ethernet, etc.) or wireless (e.g., LTE, Wi-Fi, Bluetooth, etc.) connections. The data storage may be non-removable or removable, and may include random-access memory, read-only memory, a hard disk, flash memory, a secure digital memory card, or any other type of memory storage device. In various embodiments, data or information received at or acted upon by a given module may either be retained at the given module or be accessible to the given module from a data storage of the system. For example, ID pairs may be retained in the data storage, but be accessible by an eRx evaluation module. In various embodiments, the transmit and receive modules may be combined into a single module, or remain as distinct modules.

The certification/authorization module may be configured to issue IDs and encryption keys to certified and/or authorized originator systems (e.g., FROs). IDs may also be stored at the TCRA.

In some embodiments, the TCRA system may be a component of a REMS Administrator system or network, and in some other embodiments the TCRA system may be a component of an eRx router system or network.

In some embodiments, the TCRA system may include an ETASU interface 1170 (see FIG. 3 and related discussion), which may allow a non-certified health system to generate an eRx having an encrypted RDA. For example, the RDA encryption module may operate on information received at the ETASU interface, and generate an encrypted RDA for the prescription being generated. The encrypted RDA may either be communicated back to another system for inclusion in an eRx, or an eRx including the encrypted RDA may be fully generated at the TCRA and communicated to an eRx router.

In some embodiments, the TCRA may include a reporting interface module 1180 (see FIG. 5 and related discussion), which may receive prescription reporting information back from FROs, and/or REMS Administrator-operated REMS websites and eRx router(s).

Figure 12:
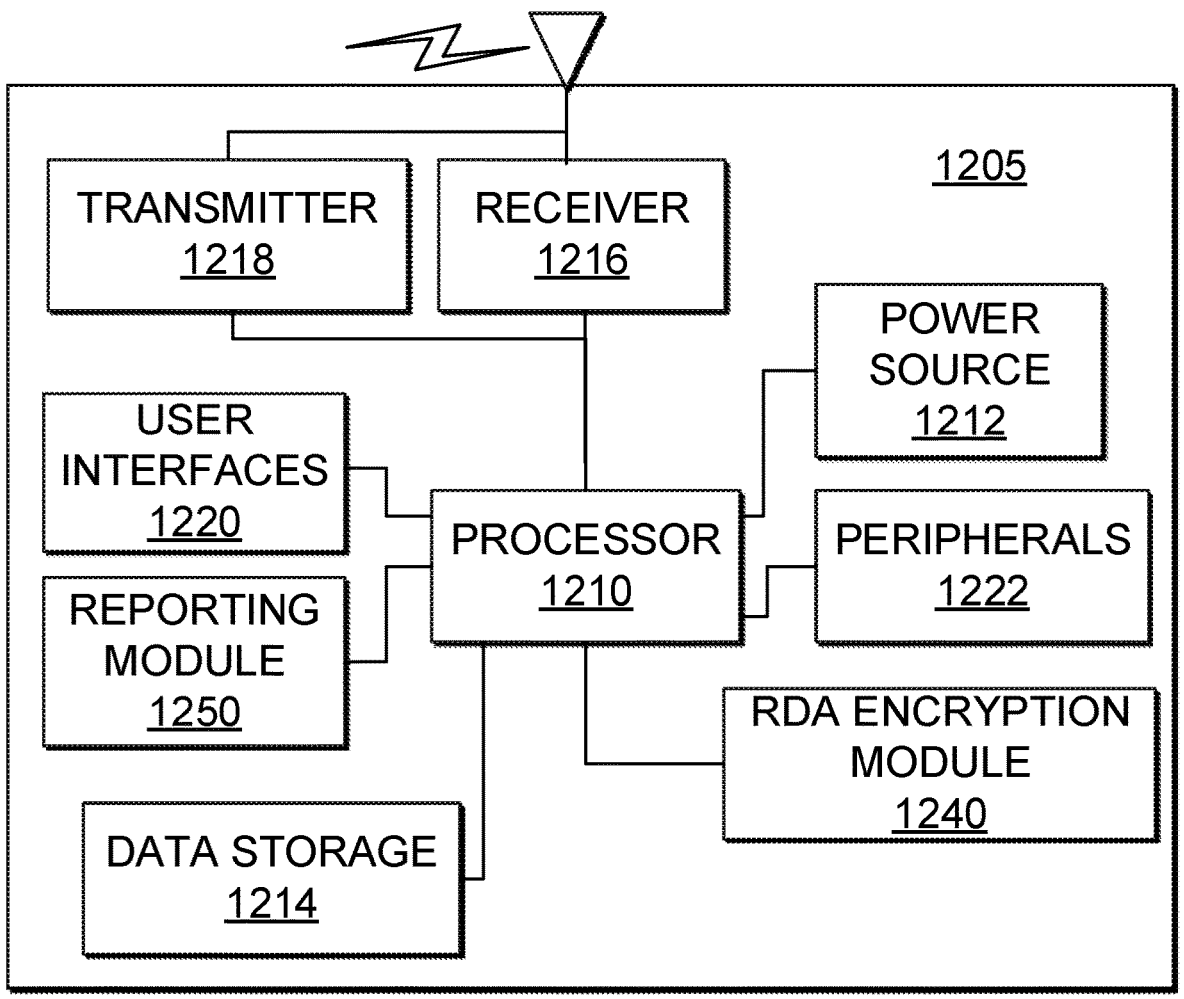
FIG. 12 illustrates an exemplary FRO system that may be employed in some embodiments.

In an embodiment, as illustrated in FIG. 12, a FRO system 1205 may comprise a processor 1210, a power source 1212 (which may be any power source suitable for the system), a data storage 1214, a receiver module 1216, and a transmitter module 1218. In some embodiments, the FRO system may comprise an RDA encryption module 1240 (may alternatively be considered an RDA or REMS processing module), and/or a reporting module 1250. In some cases, the system may comprise user interfaces 1220, such as a touchpad, a keyboard, a display, a speaker/microphone, and/or the like. In some cases, various peripherals 1222, as known to those of skill in the art, may be used with or incorporated into the system. The transmitter module and receiver module may be configured to transmit and receive signals for the system. The signals may be received over wired (e.g., ethernet, etc.) or wireless (e.g., LTE, Wi-Fi, Bluetooth, etc.) connections. The data storage may be non-removable or removable, and may include random-access memory, read-only memory, a hard disk, flash memory, a secure digital memory card, or any other type of memory storage device. In various embodiments, data or information received at or acted upon by a given module may either be retained at the given module or be accessible to the given module from a data storage of the system. For example, encryption keys may be retained in the data storage, but be accessible by an encryption module. In various embodiments, the transmit and receive modules may be combined into a single module, or remain as distinct modules.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable storage media include, but are not limited to, a read only memory (ROM), a random-access memory (RAM), a register, cache memory, semiconductor memory devices, magnetic media such as internal hard disks and removable disks, magneto-optical media, and optical media such as CD-ROM disks, and digital versatile disks (DVDs).

I claim:

1. A method, comprising:
   receiving, at an electronic prescription router (eRx-R), sets of authentication data comprising drug IDs and corresponding Risk Evaluation and Mitigation Strategies (REMS) private keys from a trusted authority;
   receiving, at the eRx-R, an electronic prescription including a prescription drug ID and an encrypted REMS Dispense Authorization (RDA) portion, the RDA portion indicating that the electronic prescription has previously been determined to be compliant with associated required REMS elements to assure safe use (REMS-ETASU);
   determining, based on the prescription drug ID, that a REMS-ETASU is in place for a drug associated with the electronic prescription and identifying a REMS private key associated with a matching drug ID from the sets of authentication data;
   decrypting the encrypted RDA portion of the electronic prescription using the REMS private key associated with the matching drug ID;
   validating a plurality of decrypted elements of the encrypted RDA portion of the electronic prescription to generate a validated electronic prescription indicating the electronic prescription has previously been determined to be compliant with associated required REMS-ETASU; and
   communicating the validated electronic prescription from the eRx-R to a pharmacy system.

2. The method of claim 1, wherein validating the plurality of decrypted elements of the encrypted RDA portion of the electronic prescription comprises validating a decrypted federated RDA originator ID and a decrypted e-prescribing network ID pair with an ID pair stored at the eRx-R.

3. The method of claim 2, wherein the ID pair is received at the eRx-R from a Trusted Central RDA Authority system at a prior time.

4. The method of claim 1, wherein validating the plurality of decrypted elements of the encrypted RDA portion of the electronic prescription comprises validating a decrypted e-prescribing network ID with an unencrypted e-prescribing network ID associated with the electronic prescription.

5. The method of claim 1, wherein validating the plurality of decrypted elements of the encrypted RDA portion of the electronic prescription comprises validating a decrypted patient ID with an unencrypted patient ID associated with the electronic prescription.

6. The method of claim 1, wherein validating the plurality of decrypted elements of the encrypted RDA portion of the electronic prescription comprises validating a decrypted prescriber ID with an unencrypted prescriber ID associated with the electronic prescription.

7. The method of claim 1, wherein validating the plurality of decrypted elements of the encrypted RDA portion of the electronic prescription comprises validating a decrypted effective date span with a current date.

8. The method of claim 1, further comprising wherein if at least one of the plurality of decrypted elements of the encrypted RDA portion of the electronic prescription cannot be validated, communicating a rejection message to a prescriber system.

9. The method of claim 1, further comprising reporting electronic prescription processing data from the eRx-R to a Trusted Central RDA Authority system.

10. The method of claim 1, wherein the electronic prescription including an encrypted RDA portion is received from a Federated RDA Originator (FRO).

11. The method of claim 10, wherein at least one element of the encrypted RDA comprises a FRO ID associated with the FRO.

12. The method of claim 1, wherein the electronic prescription including an encrypted RDA portion is received from an electronic healthcare system.

13. The method of claim 12, wherein at least one element of the encrypted RDA comprises an e-prescribing network ID associated with the electronic healthcare system.

14. The method of claim 1, wherein the electronic prescription including an encrypted RDA portion is received from a Trusted Central RDA Authority (TCRA).

15. The method of claim 14, wherein at least one element of the encrypted RDA comprises an e-prescribing network ID associated with the TCRA.

16. A system comprising a processor and a non-transitory storage medium storing instructions operative, when executed on the processor, to perform functions including:
receiving, at an electronic prescription router (eRx-R), sets of authentication data comprising drug IDs and corresponding Risk Evaluation and Mitigation Strategies (REMS) private keys from a trusted authority;
receiving, at the eRx-R, an electronic prescription including a prescription drug ID and an encrypted REMS Dispense Authorization (RDA) portion, the RDA portion indicating that the electronic prescription has previously been determined to be compliant with associated required REMS elements to assure safe use (REMS-ETASU);
determining, based on the prescription drug ID, that a REMS is in place for a drug associated with the electronic prescription and identifying a REMS private key associated with a matching drug ID from the sets of authentication data;
decrypting the encrypted RDA portion of the electronic prescription using the REMS private key associated with the matching drug ID;
validating a plurality of decrypted elements of the encrypted RDA portion of the electronic prescription to generate a validated electronic prescription indicating the electronic prescription has previously been determined to be compliant with associated required REMS-ETASU; and
communicating the validated electronic prescription from the eRx-R to a pharmacy system.

17. An electronic prescription router system comprising:
a processor;
a receiver configured to receive sets of authentication data comprising drug IDs and corresponding Risk Evaluation and Mitigation Strategies (REMS) private keys from a trusted authority and to receive an electronic prescription including a prescription drug ID and an encrypted REMS Dispense Authorization (RDA) portion, the RDA portion indicating that the electronic prescription has previously been determined to be compliant with associated required REMS elements to assure safe use (REMS-ETASU);
a non-transitory data storage medium having stored thereon instructions for an electronic prescription evaluation module, which instructions, when executed by the processor, cause the processor to be configured to validate a plurality of decrypted elements of the encrypted RDA portion of the received electronic prescription and to generate a validated electronic prescription indicating the electronic prescription has previously been determined to be compliant with associated required REMS-ETASU, wherein the plurality of decrypted elements are decrypted with a received REMS private key associated with the prescription drug ID; and
a transmitter configured to transmit the validated electronic prescription.

18. The electronic prescription router system of claim 17, wherein the non-transitory data storage medium has stored instructions for an RDA decryption module, which instructions, when executed by the processor, cause the processor to be configured to decrypt the encrypted RDA portion of the received electronic prescription.

19. The electronic prescription router system of claim 17, wherein the non-transitory data storage medium has stored instructions for a reporting module, which instructions, when executed by the processor, cause the processor to be configured to report electronic prescription processing data from the electronic prescription router to a Trusted Central RDA Authority system.

* * * * *